United States Patent
Yasuda et al.

(10) Patent No.: US 9,861,327 B2
(45) Date of Patent: Jan. 9, 2018

(54) RADIATION BLOCKING UNIT, RADIOGRAPHIC IMAGING APPARATUS, AND RADIOGRAPHIC IMAGING METHOD

(71) Applicant: FUJIFILM CORPORATION, Minato-ku, Tokyo (JP)

(72) Inventors: Hiroaki Yasuda, Kanagawa (JP); Yoshihiro Nishi, Kanagawa (JP); Haruyasu Nakatsugawa, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 211 days.

(21) Appl. No.: 14/169,157

(22) Filed: Jan. 31, 2014

(65) Prior Publication Data
US 2014/0241500 A1    Aug. 28, 2014

(30) Foreign Application Priority Data

Feb. 28, 2013   (JP) ................. 2013-040098

(51) Int. Cl.
*A61B 6/08*   (2006.01)
*A61B 6/06*   (2006.01)
(Continued)

(52) U.S. Cl.
CPC .............. *A61B 6/08* (2013.01); *A61B 6/06* (2013.01); *A61B 6/502* (2013.01); *A61B 6/025* (2013.01); *A61B 6/4035* (2013.01)

(58) Field of Classification Search
CPC .. A61B 6/06; A61B 6/08; A61B 6/502; A61B 6/025; A61B 6/4035; G21K 1/02–1/046
See application file for complete search history.

(56) References Cited

U.S. PATENT DOCUMENTS 6,778,636 B1 * 8/2004 Andrews .................. G21K 1/04
378/147
7,826,588 B2 * 11/2010 Eliasson ................ A61B 6/502
378/37

(Continued)

FOREIGN PATENT DOCUMENTS

| JP | H07-148159 A | 6/1995 |
| JP | 2008-071066  | 3/2008 |
| JP | 2011-024748  | 2/2011 |

OTHER PUBLICATIONS

English language translation of the following: Office action dated Jan. 6, 2015 from the Japanese Patent Office in a Japanese patent application corresponding to the instant patent application. This office action translation is submitted now in order to supplement the understanding of the cited references which are being disclosed in the instant Information Disclosure Statement.

(Continued)

*Primary Examiner* — Wyatt Stoffa
*Assistant Examiner* — Eliza Osenbaugh-Stewart
(74) *Attorney, Agent, or Firm* — SOLARIS Intellectual Property Group, PLLC

(57) ABSTRACT

The present invention provides a radiation blocking unit including: an attachment member that is attachable between sources and an object table surface to which radiation from a radiation source and visible light from a visible light source are emitted, the sources including the radiation source and the visible light source; a radiation blocking portion, disposed on the attachment member, that transmits the illuminated visible light to an overlapping incidence region on the object table surface in which an incidence region of the radiation and an incidence region of the visible light overlap, and that blocks the irradiated radiation outside the overlapping incidence region; and a visible light blocking portion, disposed on the attachment member, that trans- (Continued)

mits the irradiated radiation to the overlapping incidence region, and blocks the illuminated visible light outside the overlapping incidence region.

7 Claims, 25 Drawing Sheets

(51) Int. Cl.
  *A61B 6/00* (2006.01)
  *A61B 6/02* (2006.01)

(56) References Cited

U.S. PATENT DOCUMENTS

| | | | |
|---|---|---|---|
| 2006/0268409 A1* | 11/2006 | Tan | A61B 6/06 359/485.07 |
| 2010/0111261 A1* | 5/2010 | Maack | H05G 1/02 378/150 |
| 2011/0021947 A1 | 1/2011 | Nakayama et al. | |
| 2011/0075799 A1* | 3/2011 | Okada | A61B 6/022 378/41 |
| 2012/0183126 A1* | 7/2012 | Cho | G21K 1/04 378/150 |

OTHER PUBLICATIONS

Extended European Search Report dated May 27, 2014 from the EPO in an European patent application corresponding to the instant patent application.

English language translation of the following: Office action dated Sep. 1, 2015 from the Japanese Patent Office in a Japanese patent application corresponding to the instant patent application.

\* cited by examiner

RADIATION BLOCKING UNIT, RADIOGRAPHIC IMAGING APPARATUS, AND RADIOGRAPHIC IMAGING METHOD

CROSS-REFERENCE TO RELATED APPLICATION

This application claims priority under 35 USC 119 from Japanese Patent Application No. 2013-040098, filed on Feb. 28, 2013, the disclosure of which is incorporated by reference herein.

BACKGROUND OF THE INVENTION

Field of the Invention

The present invention relates to a radiation blocking unit, a radiographic imaging apparatus, and a radiographic imaging method. In particular, the present invention relates to a radiographic imaging apparatus in which an incidence region of radiation is indicated by visible light, a radiation blocking unit that is attachable to the radiographic imaging apparatus, and a radiographic imaging method.

Description of the Related Art

Mammography machines for the early detection of breast cancer, for example, are known as medical radiographic imaging apparatus. A mammography machine captures a radiographic image of a breast, serving as an imaging target of an examinee, in a state in which the breast is squeezed between an object table surface of an object table and a compression plate and the breast is compressed by the compression plate. A radiation detection panel is built into the object table, and radiation transmitted through the breast is detected in the radiation detection panel.

U.S. Pat. No. 7,826,588 discloses a device and method for generating digital X-ray images of a sample. In this device and method, a sample of tissue excised from a breast is placed on a support plate disposed above a biopsy unit, with the breast remaining squeezed and compressed between a detector and the biopsy unit. The sample is placed above an unused region of an object table surface of the detector. Then, the sample is irradiated with X-ray radiation, whereby an X-ray image of the sample is obtained without exposing the breast to unnecessary X-ray radiation.

As disclosed in Japanese Patent Application Laid-Open (JP-A) No. H07-148159, for example, in order to check an incidence region of radiation to be emitted to an examination object, a radiographic imaging apparatus is disposed with a light aiming mechanism that emits visible light to an incidence region that is the same as the incidence region of the radiation. In the device and method disclosed in U.S. Pat. No. 7,826,588, in order to obtain an X-ray image of the sample, the incidence region of the X-ray radiation is changed to an unused region of the object table surface of the detector outside the breast in the compressed state. The changing of the incidence region of the X-ray radiation is accomplished by moving a blocking plate disposed in a collimator box. The places where an X-ray source that emits X-ray radiation and a visible light source that emits visible light are disposed are different, so when the X-ray radiation and the visible light pass through a slit in the blocking plate, the incidence region, on the object table surface, of the radiation that has been emitted from the X-ray source and the incidence region, on the object table surface, of the visible light that has been emitted from the visible light source do not coincide. For this reason, there has been room for improvement.

SUMMARY OF THE INVENTION

The present invention provides a radiation blocking unit, a radiographic imaging apparatus, and a radiographic imaging method that may improve the precision with which an incidence region, on an object table surface, of radiation irradiated from a radiation source and an incidence region, on the object table surface, of visible light illuminated from a visible light source coincide.

A first aspect of the invention is a radiation blocking unit including: an attachment member that is attachable between sources and an object table surface to which radiation from a radiation source and visible light from a visible light source are emitted, the sources including the radiation source and the visible light source; a radiation blocking portion, disposed on the attachment member, that transmits the illuminated visible light to an overlapping incidence region on the object table surface in which an incidence region of the radiation and an incidence region of the visible light overlap, and that blocks the irradiated radiation outside the overlapping incidence region; and a visible light blocking portion, disposed on the attachment member, that transmits the irradiated radiation to the overlapping incidence region, and blocks the illuminated visible light outside the overlapping incidence region.

In the radiation blocking unit according to the first aspect, the attachment member is attachable between the sources and the object table surface, and the radiation blocking portion and the visible light blocking portion are disposed on the attachment member. Here, the radiation blocking portion transmits the visible light illuminated to the overlapping incidence region on the object table surface in which the incidence region of the radiation and the incidence region of the visible light overlap and blocks the radiation irradiated outside the overlapping incidence region. The visible light blocking portion transmits the radiation irradiated to the overlapping incidence region and blocks the visible light illuminated outside the overlapping incidence region. For this reason, the radiation and the visible light illuminated outside the overlapping incidence region are blocked, so only the radiation and the visible light illuminated to the overlapping incidence region are transmitted to the object table surface.

In a second aspect of the present invention, in the above aspect, with respect to the radiation irradiated and the visible light illuminated to the object table surface outside the boundary of an examination object, the radiation blocking portion may block the irradiated radiation outside the overlapping incidence region and the visible light blocking portion may block the illuminated visible light outside the overlapping incidence region.

According to the radiation blocking unit according to the second aspect, the precision with which the incidence regions of the radiation and the visible light illuminated to the object table surface outside the boundary of the examination object coincide is improved. For this reason, a radiographic image may be imaged outside the boundary of the examination object in a state in which the examination object is on the object table surface. For example, a tissue or organ sample may be collected from the examination object in a state in which the examination object is already positioned on the object table surface for imaging, and a radiographic image of the collected sample can be imaged outside the boundary of the examination object with the examination object remaining in the positioned state.

In a third aspect of the present invention, in the above aspects, the attachment member may include a through portion that defines the incidence region of at least one of the radiation and the visible light, and either the radiation blocking portion or the visible light blocking portion may be disposed on the attachment member via a position adjusting mechanism that adjusts the position of the either the radiation blocking portion or the visible light blocking portion.

According to the radiation blocking unit according to the third aspect, the attachment member has the through portion, and either one of the radiation blocking portion and the visible light blocking portion is disposed on the attachment member via the position adjusting mechanism. Here, the position adjusting mechanism can adjust the position of the either one of the radiation blocking portion and the visible light blocking portion. For this reason, the position of the incidence region of either one of the radiation and the visible light illuminated outside the overlapping incidence region can be adjusted by the position adjusting mechanism, so the precision with which the incidence region of the radiation and the incidence region of the visible light coincide may be improved even more.

In a fourth aspect of the present invention, in the first or second aspect, the attachment member may include a through portion that defines the incidence region of at least one of the radiation or the visible light, and both the radiation blocking portion and the visible light blocking portion may be disposed on the attachment member via position adjusting mechanisms that adjust the positions of both the radiation blocking portion and the visible light blocking portion.

According to the radiation blocking unit according to the fourth aspect, the attachment member has the through portion, and both the radiation blocking portion and the visible light blocking portion are disposed on the attachment member via the position adjusting mechanisms. Here, the position adjusting mechanisms can adjust the positions of both the radiation blocking portion and the visible light blocking portion. For this reason, the positions of the incidence regions of the radiation and the visible light illuminated outside the overlapping incidence region can be adjusted by the position adjusting mechanisms, so the precision with which the incidence region of the radiation and the incidence region of the visible light coincide may be further improved.

In a fifth aspect of the present invention, in the third or fourth aspect, the attachment member may block at least one of the radiation from the radiation source and the visible light from the visible light source.

According to the radiation blocking unit according to the fifth aspect, the attachment member can be used as a blocking portion that blocks at least either one of the radiation and the visible light. For this reason, the configuration that moves the incidence region of at least either one of the radiation and the visible light may be simplified. For example, the configuration of a blocking plate moving mechanism for moving and changing the incidence region of the radiation inside a collimator box is simplified.

In a sixth aspect of the present invention, in the third or fourth aspect, the attachment member may be formed of a rolled steel plate that blocks the radiation from the radiation source and the visible light from the visible light source.

In the radiation blocking unit according to the sixth aspect, the attachment member is formed of a rolled steel plate, and the radiation from the radiation source and the visible light from the visible light source are blocked by the rolled steel plate. For this reason, the configuration that moves the incidence region of at least either one of the radiation and the visible light may be simplified. Furthermore, because the rolled steel plate is a general-purpose material, the radiation blocking unit may be easily manufactured and manufacturing costs may be reduced.

In a seventh aspect of the present invention, in the above aspects, the radiation blocking portion may be formed of lead glass and the visible light blocking portion may be formed of carbon-glass fiber.

According to the radiation blocking unit according to the seventh aspect, the radiation blocking portion is formed of lead glass and the visible light blocking portion is formed of carbon-glass fiber. For this reason, the radiation blocking unit may is easily manufactured because lead glass and carbon-glass fiber are both general-purpose materials.

An eighth aspect of the present invention is a radiographic imaging apparatus including: an object table that has an object table surface; a radiation source disposed above the object table surface; a radiation emitting section that controls the emission of radiation from the radiation source; a visible light source disposed above the object table surface at a position different from that of the radiation source; a visible light emitting section that controls the emission of visible light from the visible light source; a blocking plate, disposed between the object table surface and the radiation source, that defines an incidence region of the radiation from the radiation source on the object table surface; a blocking plate moving section that moves the blocking plate in a direction intersecting the direction in which the radiation is emitted so as to move the incidence region of the radiation on the object table surface; a radiation blocking portion, disposed between the object table surface and the blocking plate, that transmits the illuminated visible light to an overlapping incidence region on the object table surface, in which the incidence region of the radiation and an incidence region of the visible light overlap, and that blocks the irradiated radiation outside the overlapping incidence region; and a visible light blocking portion, disposed between the object table surface and the blocking plate, that transmits the irradiated radiation to the overlapping incidence region, and blocks the illuminated visible light outside the overlapping incidence region.

In the radiographic imaging apparatus according to the eighth aspect, the visible light from the visible light source is emitted to the object table surface of the object table by the visible light emitting section, and the incidence region of the radiation is indicated by the incidence region of the visible light. The radiation emitting section controls the emission of the radiation from the radiation source, and the radiation from the radiation source is emitted to the object table surface through the blocking plate. The blocking plate can be moved, by the blocking plate moving section, in a direction intersecting the direction in which the radiation is emitted, and when the blocking plate moves, the incidence region of the radiation on the object table surface moves.

Here, the radiation blocking portion and the visible light blocking portion are disposed between the object table surface and the blocking plate. The radiation blocking portion transmits the visible light illuminated to the overlapping incidence region on the object table surface in which the incidence region of the radiation and the incidence region of the visible light overlap and blocks the radiation irradiated outside the overlapping incidence region. The visible light blocking portion transmits the radiation irradiated to the overlapping incidence region and blocks the visible light illuminated outside the overlapping incidence region. For this reason, the radiation and the visible light illuminated outside the overlapping incidence region are blocked, so only the radiation and the visible light illuminated to the overlapping incidence region are transmitted to the object table surface. Consequently, even if the incidence region of the radiation is moved in accompaniment with the movement of the blocking plate, the incidence region of the radiation and the incidence region of the visible light coincide.

In a ninth aspect of the present invention, in the eighth aspect, may further include a biopsy unit, disposed between the object table surface and the blocking plate, that examines tissue.

In the radiographic imaging apparatus according to the ninth aspect, the biopsy unit is disposed between the object table surface and the blocking plate. For this reason, tissue can be examined by the biopsy unit. For example, the radiographic imaging apparatus may use the biopsy unit to capture a radiographic image of the tissue outside the boundary of an examination object in a state in which the examination object is on the object table surface.

In a tenth aspect of the present invention, in the eighth or ninth aspect, may further include a compression plate disposed between the object table surface and the blocking plate, that compresses an examination object.

In the radiographic imaging apparatus according to the tenth aspect, the compression plate is disposed between the object table surface and the blocking plate, and the compression plate can compress the examination object. If, for example, the examination object is a breast, the radiographic imaging apparatus may be applied to a mammography machine.

An eleventh aspect of the present invention is a radiographic imaging method including: detecting a position of an examination object on an object table surface; setting a tissue observation region outside the boundary of the examination object on the object table surface based on the position of the examination object; emitting, from a visible light source to the observation region, visible light that indicates an incidence region of radiation, and blocking the illuminated visible light outside the observation region; emitting the radiation from a radiation source to the observation region and blocking the irradiated radiation outside the observation region; and generating a radiographic image of the tissue on the basis of the radiation that has been emitted to the observation region.

In the radiographic imaging method according to the eleventh aspect, when the position of the examination object on the object table surface is detected, the tissue observation region is set outside the boundary of the examination object on the object table surface on the basis of the position of the examination object. The visible light indicating the incidence region of the radiation is emitted from the visible light source to the observation region, and then the radiation is emitted to the observation region. The radiographic image of the tissue is generated on the basis of the radiation that has been emitted to the observation region.

Here, the visible light illuminated outside the observation region is blocked, and the radiation irradiated outside the observation region is blocked. For this reason, the visible light and the radiation are emitted only to the observation region, so the incidence region of the visible light and the incidence region of the radiation coincide.

According to the above aspects, the radiation blocking unit, the radiographic imaging apparatus, and the radiographic imaging method according to the present invention may improve the precision with which a incidence region, on an object table surface, of radiation irradiated from a radiation source and a incidence region, on the object table surface, of visible light illuminated from a visible light source coincide.

BRIEF DESCRIPTION OF THE DRAWINGS

Exemplary embodiments of the present invention will be described in detail based on the following figures, wherein.

DETAILED DESCRIPTION OF THE INVENTION

Figure 1:
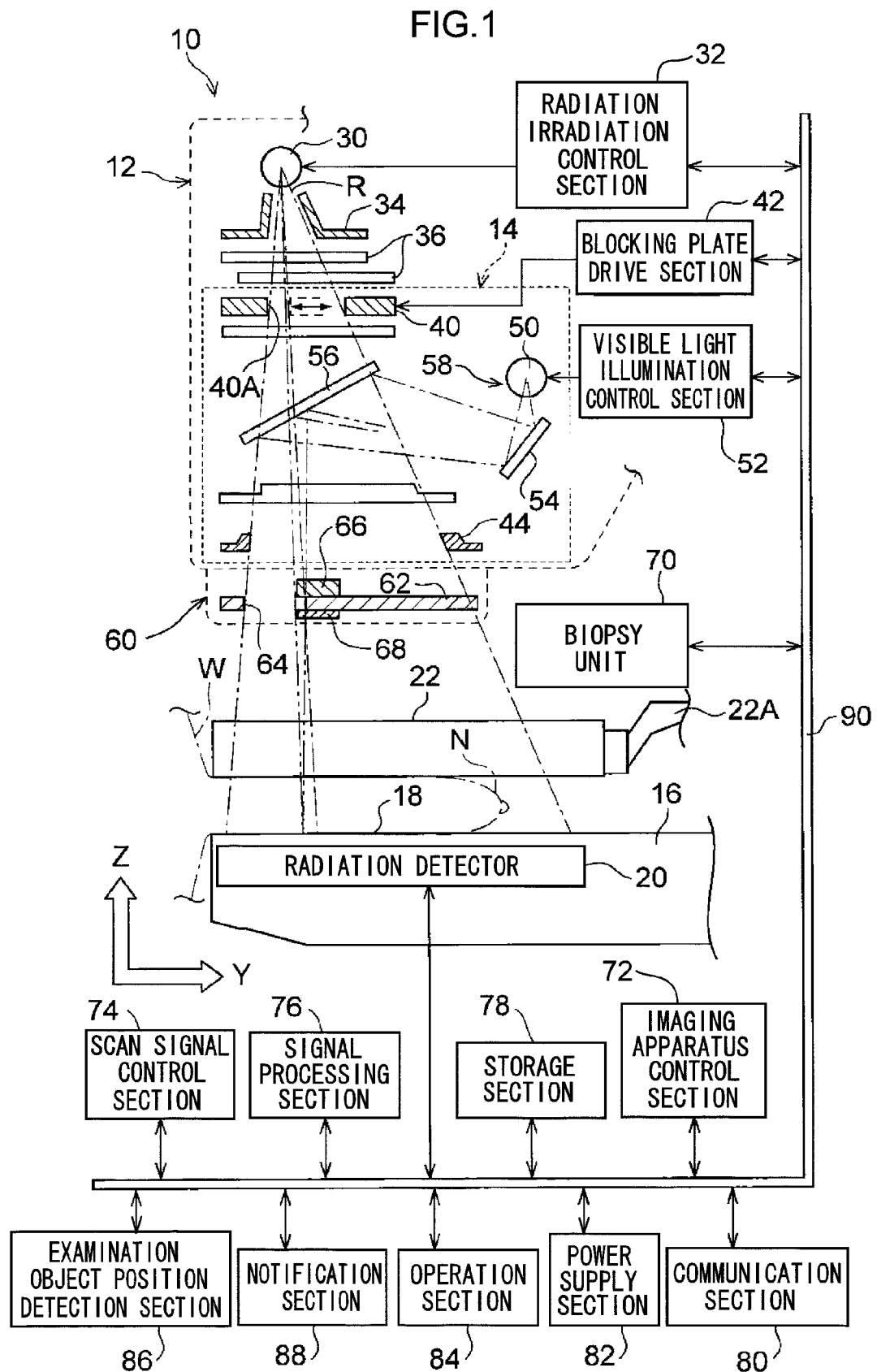
FIG. 1 is a block configuration diagram describing the overall configuration of a radiographic imaging apparatus according to a first exemplary embodiment of the present invention.

Exemplary embodiments according to the present invention will be described below with reference to the attached drawings. Identical reference signs are assigned to constituent elements having identical functions in the drawings, and redundant description of those constituent elements is appropriately omitted. Furthermore, the direction appropriately shown in the drawings and denoted by reference sign X is a direction heading from the left side to the right side as seen from the perspective of an examinee (a person undergoing imaging) facing the radiographic imaging apparatus in order to undergo radiographic imaging. Likewise, the direction denoted by reference sign Y is a direction heading from the front side (chest wall side) of the examinee toward the back side of the radiographic imaging apparatus, and the direction denoted by reference sign Z is a direction heading from the lower side in the area of the feet of the examinee toward the upper side of the radiographic imaging apparatus. That is, reference signs X, Y, and Z denote directions coinciding with the x-axis, the y-axis, and the z-axis of an xyz coordinate system.

[First Exemplary Embodiment]

A first exemplary embodiment of the present invention will be described using FIG. 1 to FIG. 16. The first exemplary embodiment describes an example where the present invention is applied as a radiographic imaging apparatus to a mammography machine.

Figure 2:
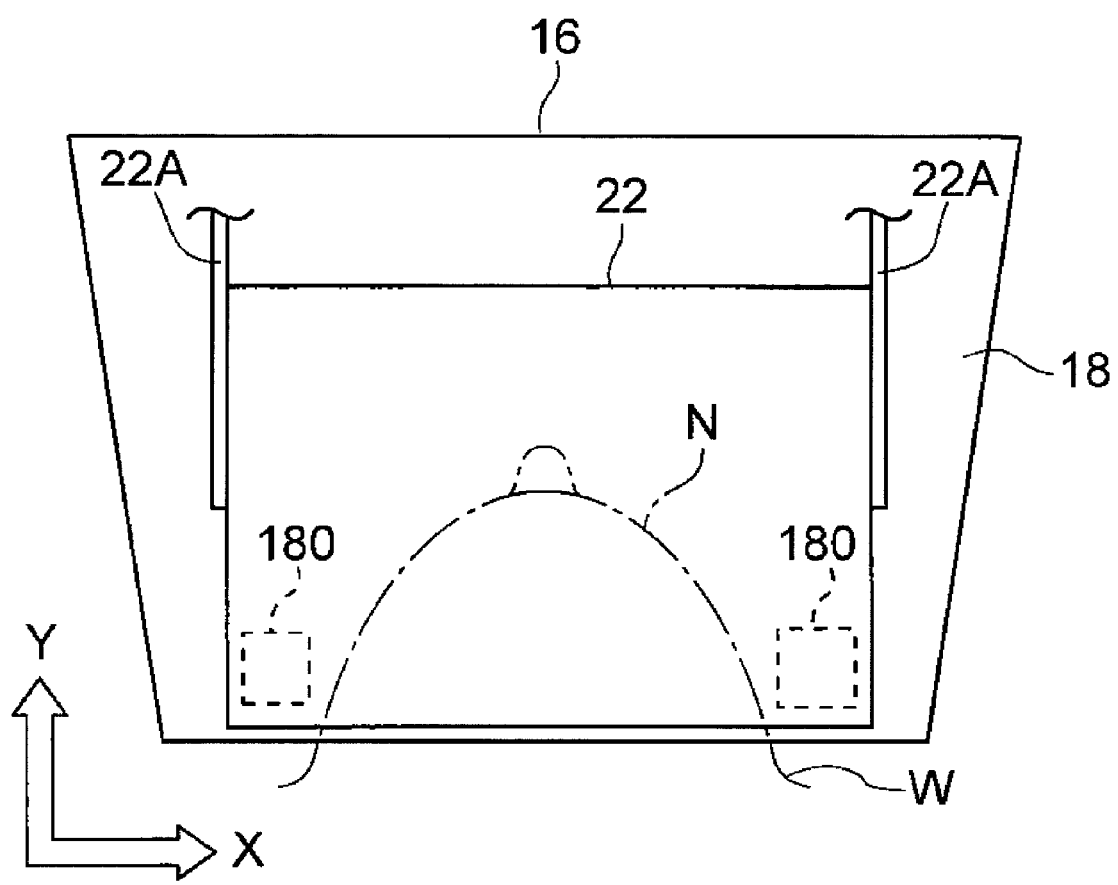
FIG. 2 is a plan view of an object table surface and a compression plate of the radiographic imaging apparatus shown in FIG. 1.

As shown in FIG. 1 and FIG. 2, a radiographic imaging apparatus 10 according to the first exemplary embodiment is equipped with an object table 16, an object table surface 18 that is disposed on the upper portion of the object table 16 and has a generally rectangular shape as seen in a plan view, and a radiation emitting section 12 that is disposed above the object table surface 18, faces the object table surface 18, and is spaced apart from the object table surface 18. A compression plate 22 that can be moved in the up and down direction is disposed between the object table surface 18 and the radiation emitting section 12. The left side shown in FIG. 1 is the chest wall side of an examinee (a person undergoing imaging) W, and the right side shown in FIG. 1 is the back side of the radiographic imaging apparatus 10. Furthermore, the lower side shown in FIG. 2 is the chest wall side, and the upper side shown in FIG. 2 is the back side. The compression plate 22 is supported by support arms 22A disposed on the back side, and the support arms 22A are rotatably attached to a non-illustrated casing of the radiographic imaging apparatus 10. Because of this, the compression plate 22 can be inclined in the clockwise direction and the counter-clockwise direction in FIG. 1 using the support arm 22A side as a rotational center. The radiographic imaging apparatus 10 can capture a radiographic image of a breast N in a state in which the breast N is squeezed and compressed between the object table surface 18 and the compression plate 22, which can be set to various angles of inclination. Furthermore, the object table 16, the compression plate 22, and the radiation emitting section 12 can rotate in the clockwise direction and the counter-clockwise direction as seen from the perspective of the examinee W, so that the radiographic imaging apparatus 10 can perform tomosynthesis imaging.

Inside the radiation emitting section 12, a radiation source 30 and a collimator box 14 are disposed as main components. The radiation source 30 is a medical X-ray source in the present exemplary embodiment. The radiation source 30 is connected to a radiation irradiation control section 32. The radiation irradiation control section 32 controls the emission of radiation R from the radiation source 30 on the basis of exposure conditions. The radiation irradiation control section 32 is connected to a non-illustrated console via a common bus 90 and a communication section 80, and various types of information such as the exposure conditions are input from the console to the radiation irradiation control section 32. Here, the exposure conditions include at least information including tube voltage, tube current, and duration of exposure, for example. The radiation R is not limited to X-ray radiation and at least includes gamma-ray radiation, electron beams, neutron beams, photon beams, and heavy particle beams used in medical procedures.

A first blocking portion 34 serving as an extra-focal radiation reducing vane is disposed below the radiation source 30 on the object table surface 18 side. The first blocking portion 34 allows the radiation R emitted in the direction of the object table surface 18 to pass through and blocks the radiation R traveling in other directions. Filters 36 are disposed below the first blocking portion 34. The filters 36 are configured by sequentially putting together Mo, Rh, Al, and Ag films, for example, in the film planar direction. The filters 36 can be moved in the film planar direction so that any of the films can be selected. Radiation R having the necessary characteristics is obtained by allowing the radiation R to be transmitted through the selected films of the filters 36.

The collimator box 14 is disposed below the filters 36. Inside the collimator box 14, a blocking plate 40 serving as a lower vane is disposed in the upper portion on the radiation source 30 side, and a second blocking portion 44 serving as a beam limiting vane is disposed in the lower portion on the object table surface 18 side. The blocking plate 40 is configured by a plate-like member that blocks the radiation R and is disposed with a through portion 40A that allows the radiation R to pass through. The blocking plate 40 is connected to a blocking plate drive section 42 and can move in a direction intersecting (here, a planar direction orthogonal to) the direction in which the radiation R is emitted. That is, the through portion 40A in the light-blocking plate 40 moves parallel to the object table surface 18, so that the incidence region of the radiation R on the object table surface 18 can be moved. The blocking plate drive section 42 is connected to an imaging apparatus control section 72 and an operation section 84 via the common bus 90, and the blocking plate 40 can be moved by an operation from the operation section 84. The second blocking portion 44 here is fixed inside the collimator box 14 and decides the useful beam of the radiation R.

A light aiming section 58 is disposed inside the collimator box 14. The light aiming section 58 uses visible light L to indicate the incidence region of the radiation R on the object table surface 18. The light aiming section 58 is equipped with a visible light source 50 that emits visible light L, a visible light illumination control section 52 that is connected to the visible light source 50 and controls the lighting-up of the visible light source 50, and optical mirrors 54 and 56. The visible light illumination control section 52 is connected to the imaging apparatus control section 72 and the operation section 84 via the common bus 90, so that the light aiming section 58 can be controlled by an operation from the operation section 84. In the first exemplary embodiment, the visible light source 50 is disposed on the back side, and the visible light L emitted from the visible light source 50 is reflected by the optical mirror 54 and guided to the optical mirror 56 disposed in the useful beam. The optical mirror 56 reflects the visible light L toward the object table surface 18. The optical mirror 56 transmits the radiation R and reflects the visible L onto the object table surface 18 so that the visible light L coincides with the incidence region of the radiation R.

As shown in FIG. 1, a radiation blocking unit 60 attachable to the bottom wall of the radiation emitting section 12 is disposed between the radiation emitting section 12 (specifically, the radiation source 30 and the visible light source 50) and the object table surface 18. The radiation blocking unit 60 has the function of deflecting the directions in which the radiation R and the visible light L are emitted and causing the incidence regions of both to coincide with the object table surface 18 (end portions of the object table surface 18) outside the boundary of the breast N in the compressed state between the compression plate 22 and the object table surface 18. In the radiographic imaging apparatus 10 according to the first exemplary embodiment, a biopsy unit 70 is disposed between the radiation emitting section 12 and the object table surface 18. The biopsy unit 70 collects a sample by excising some tissue from the breast N. By utilizing the radiation blocking unit 60 so that the radiation R is emitted outside the boundary of the breast N, the radiographic imaging apparatus 10 can capture a radiographic image of the sample outside the boundary of the breast N with the breast N remaining in the compressed state. Here, saying that the radiation blocking unit 60 is "attachable" includes both a case where the radiation blocking unit 60 is semi-permanently attached to the radiation emitting section 12 by fastening section such as bolts or screws, for example, and a case where the radiation blocking unit 60 is detachably attached to the radiation emitting section 12.

As shown in FIG. 1 and FIG. 3 to FIG. 5, the radiation blocking unit 60 has, as main components, an attachment member 62 that is attachable to the radiation emitting section 12, radiation blocking portions 66 that are disposed on the attachment member 62, and visible light blocking portions 68 that are likewise disposed on the attachment member 62. The attachment member 62 is not limited to a particular shape, and here it is configured by a rectangular plate as seen in a plan view. In the first exemplary embodiment, a material and thickness that transmit neither the radiation R nor the visible light L are selected for the attachment member 62. For example, the attachment member 62 is made of a rolled steel plate having a thickness of 2 mm or greater. Through portions 64 that define the incidence regions of the radiation R and the visible light L are disposed in the attachment member 62 as a right and left pair on the chest wall side as seen from the perspective of the examinee W. Here, the through portions 64 are configured as rectangular through holes as seen in a plan view.

Figure 5:
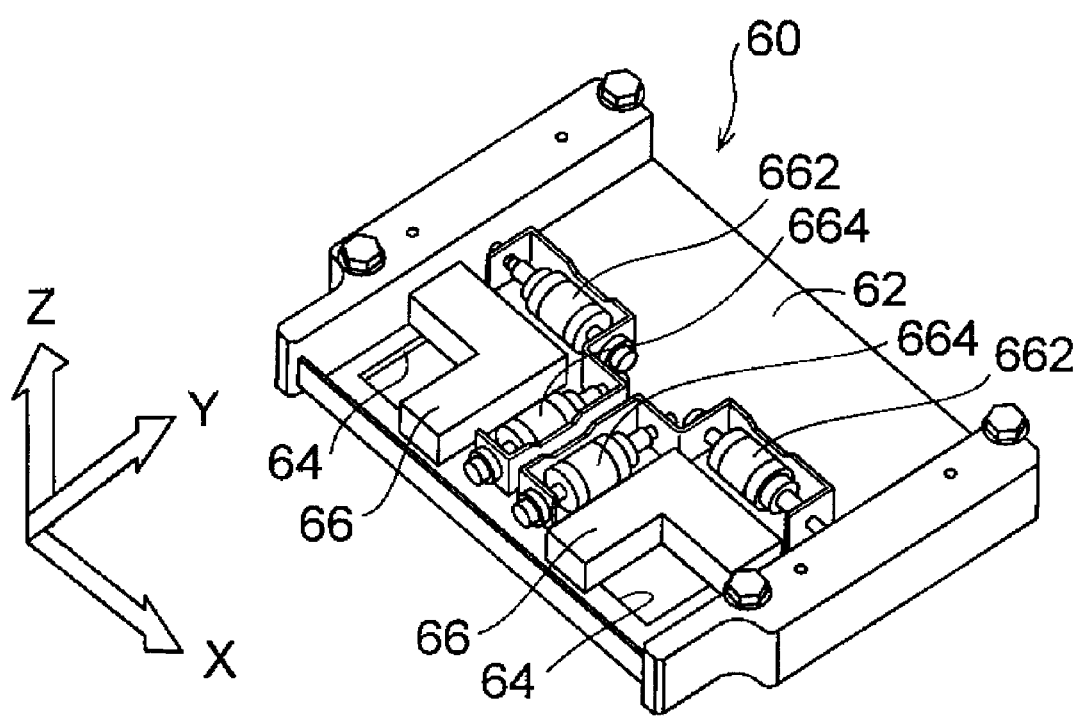
FIG. 5 is an enlarged perspective view showing, as seen looking leftward and downward from above, the radiation blocking unit shown in FIG. 3 and FIG. 4.
Figure 6:
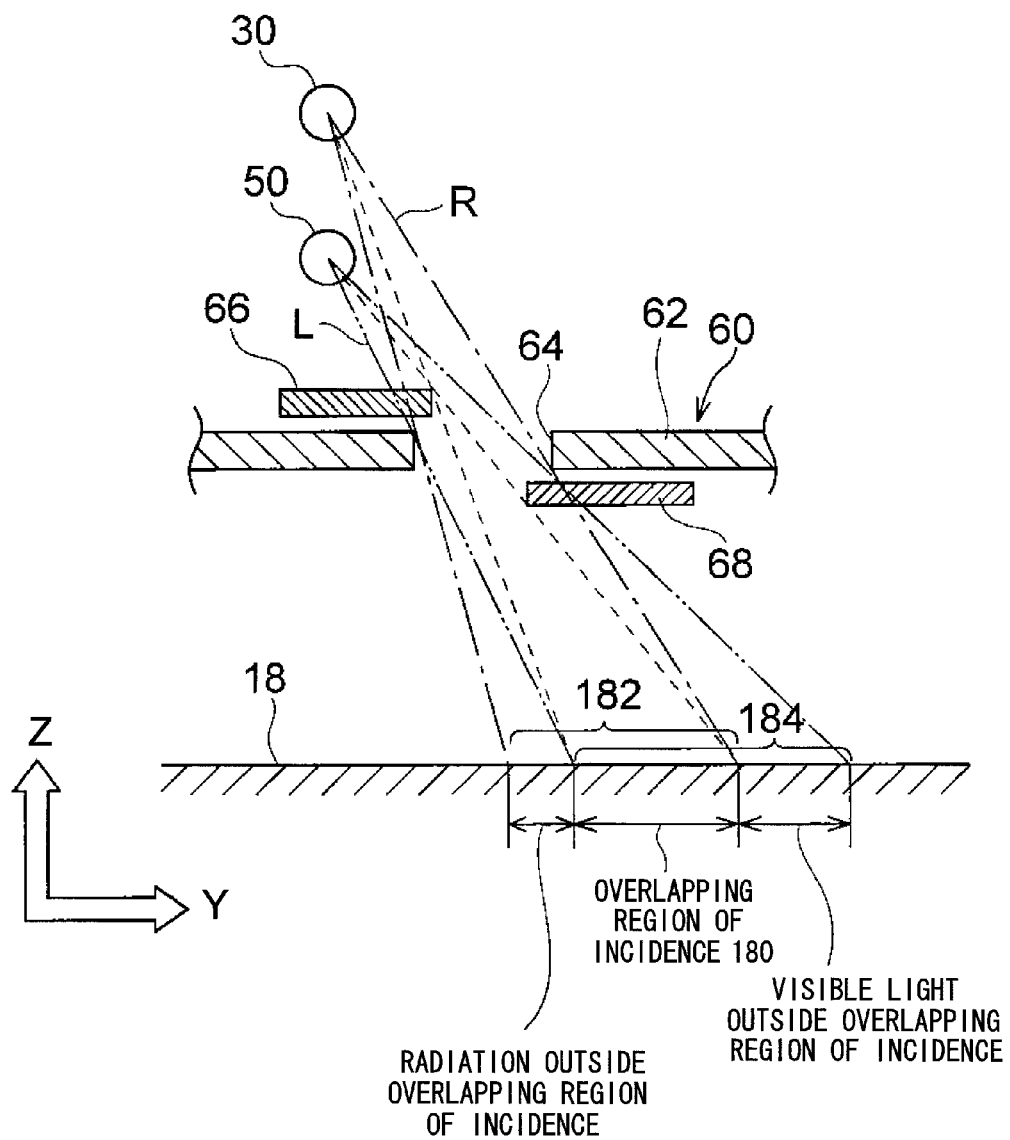
FIG. 6 is a conceptual diagram describing a method of adjusting incidence regions of radiation and visible light in the radiographic imaging apparatus according to the first exemplary embodiment.

Particularly, as shown in FIG. 5, the radiation blocking portions 66 are plurally disposed on the top surface of the attachment member 62 on the radiation emitting section 12 side in correspondence to the right and left pair of through portions 64. The radiation blocking portions 66 are formed in L shapes as seen in a plan view and cover parts of the through portions 64, including the backside edge portions of the through portions 64 and the mutually opposing inside edge portions of the right and left pair of through portions 64. Here, as shown in FIG. 6, incidence regions 182 of the radiation R that has been emitted through the through portions 64 from the radiation source 30 and incidence regions 184 of the visible light L that has been emitted through the through portions 64 from the visible light source 50 in order to indicate those incidence regions 182 are formed on the object table surface 18. Overlapping incidence regions 180 in which the incidence regions 182 and the incidence regions 184 overlap are used as observation regions for imaging a radiographic image of the sample collected by the biopsy unit 70 and for observing the sample. The radiation blocking portions 66 have the function of transmitting the visible light L emitted to the overlapping incidence regions 180 and blocking the radiation R emitted outside the overlapping incidence regions 180. Lead glass, for example, is used for the radiation blocking portions 66.

Position adjusting mechanisms 662 and position adjusting mechanisms 664 are disposed for each of the right and left pair of radiation blocking portions 66 as seen from the perspective of the examinee W. Although detailed illustration is omitted, the position adjusting mechanisms 662 have worm gears, which are attached to the attachment member 62 in such a way as to be rotatable taking the right and left direction (the X direction) as an axial direction, and racks, which mesh with the worm gears and are attached to the radiation blocking portions 66. In other words, the position adjusting mechanisms 662 can adjust the positions of the radiation blocking portions 66 in the right and left direction by causing the worm gears to rotate. Likewise, the position adjusting mechanisms 664 have worm gears, which are attached to the attachment member 62 in such a way as to be rotatable taking the front and rear direction (the Y direction) as an axial direction, and racks, which mesh with the worm gears, and are attached to the radiation blocking portions 66. The position adjusting mechanisms 664 can adjust the positions of the radiation blocking portions 66 in the front and rear direction, in the planar direction of the plate configuring the attachment member 62, by causing the worm gears to rotate.

Figure 3:
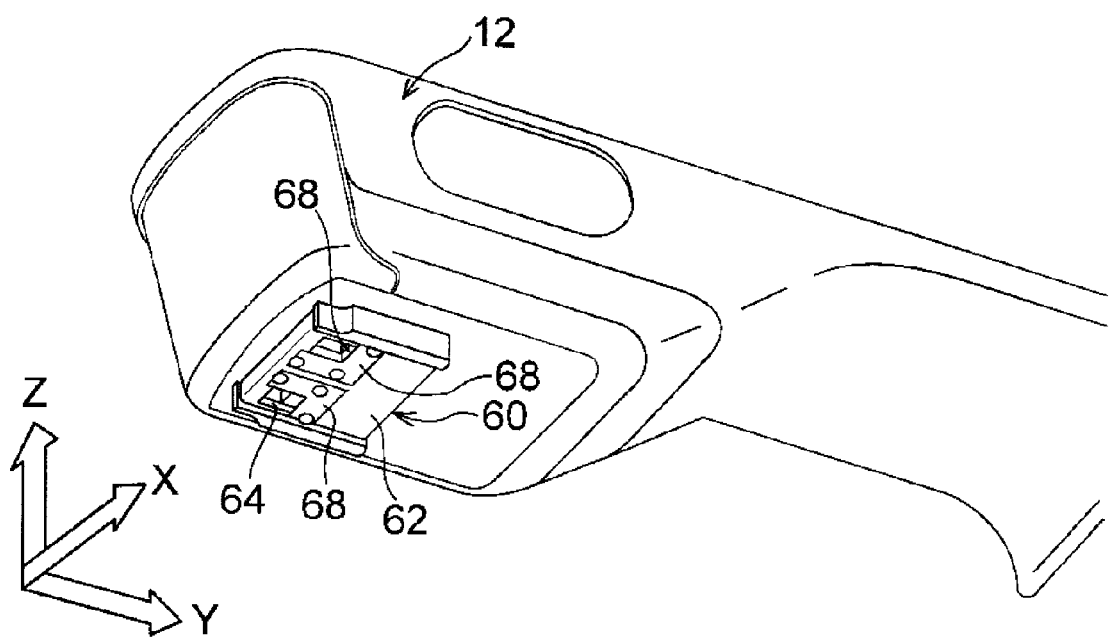
FIG. 3 is a perspective view showing, as seen looking leftward and upward from below, a radiation emitting section and a radiation blocking unit of the radiographic imaging apparatus shown in FIG. 1.
Figure 4:
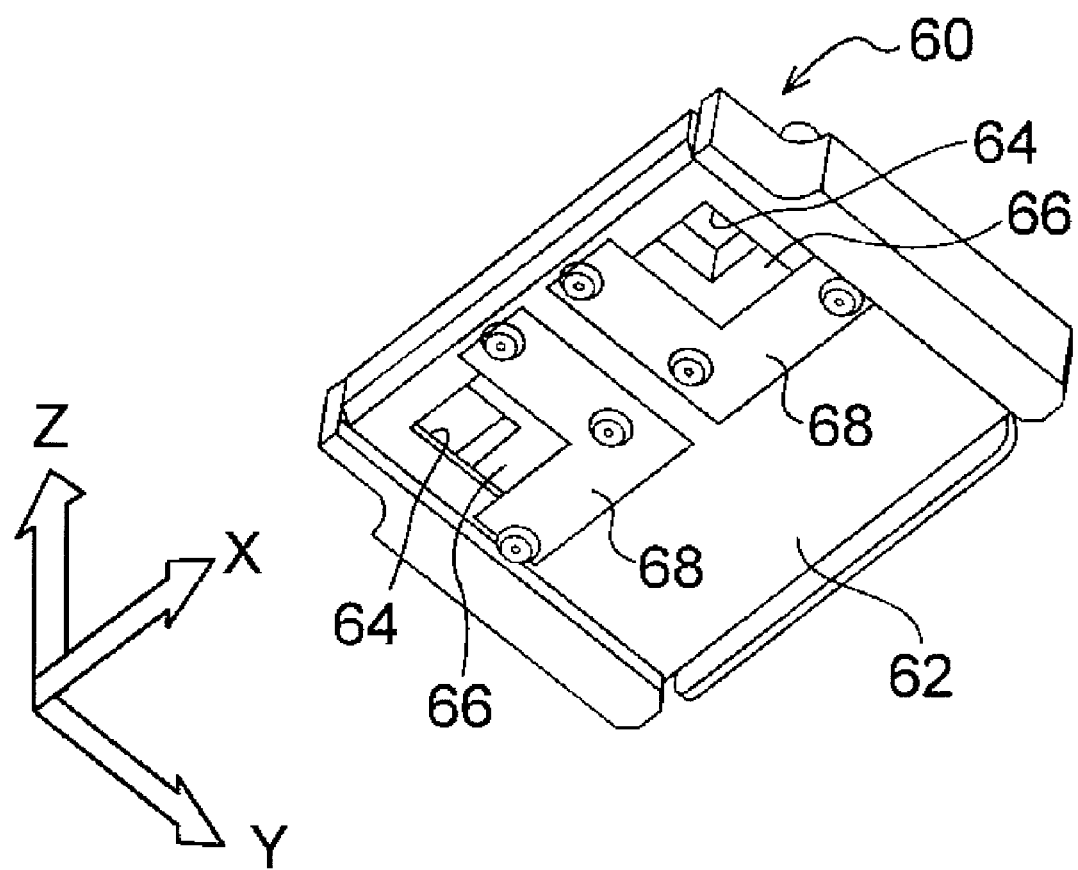
FIG. 4 is an enlarged perspective view showing, as seen from the same direction as the direction shown in FIG. 3, the radiation blocking unit shown in FIG. 3.

As shown in FIG. 3 and FIG. 4, the visible light blocking portions 68 are plurally disposed on the bottom surface of the attachment member 62 on the object table surface 18 side in correspondence to the right and left pair of through portions 64. Like the radiation blocking portions 66, the visible light blocking portions 68 are formed in L shapes as seen in a plan view and cover parts of the through portions 64, including the backside edge portions of the through portions 64 and the mutually opposing inside edge portions of the right and left pair of through portions 64. As shown in FIG. 6, the visible light blocking portions 68 have the function of transmitting the radiation R emitted to the overlapping incidence regions 180 and blocking the visible light L emitted outside the overlapping incidence regions 180. Carbon-glass fiber, for example, is used for the visible light blocking portions 68. As shown in FIG. 3 and FIG. 4, in the first exemplary embodiment, the visible light blocking portions 68 are fixed to the attachment member 62 by fastening section such as bolts or screws. However, the visible light blocking portions 68 may also be configured in such a way that their positions can be adjusted by disposing the position adjusting mechanisms 662 and 664.

In the radiation blocking unit 60 shown in FIG. 3 to FIG. 5, the right and left pair of through portions 64 are disposed in the attachment member 62, and the radiation blocking portions 66 and the visible light blocking portions 68 are disposed on the through portions 64. For this reason, in the radiographic imaging apparatus 10, observation regions can be set outside the boundary on the left side or outside the boundary on the right side of the breast N as seen from the perspective of the examinee W.

As shown in FIG. 1, in the radiographic imaging apparatus 10, a radiation detector (a radiation detection panel) 20 is disposed inside the object table 16. The radiation detector 20 is not limited to a particular type, and in the first exemplary embodiment a direct-conversion-type flat panel detector (FPD) is employed. The radiation detector 20 is irradiated with the radiation R, which is transmitted through the compression plate 22, the breast N, and the object table surface 18 from the radiation emitting section 12 and carries image information of the breast N in its detection elements, and generates charge signals. The detection elements are selected by signals from a scan signal control section (a gate line control section) 74, and the charge signals generated by the detection elements are read out to a signal processing section 76. The signal processing section 76 converts the charge signals into voltage signals and thereafter generates radiographic image information.

The radiographic image information generated by the signal processing section 76 is stored in a storage section 78 and is transmitted to the non-illustrated console or the like via the communication section 80. Actions such as the generation, storage, and transmission of the radiographic image information are executed via the imaging apparatus control section 72 in accordance with an operation from the operation section 84. The imaging apparatus control section 72 controls each section, such as the signal processing section 76 and the storage section 78, and is connected to each section via the common bus 90. Furthermore, a power supply section 82 that supplies power to each section and a later-described examination object position detection section 86 and notification section 88 are connected to the common bus 90.

Next, a radiographic imaging method in the radiographic imaging apparatus 10 (specifically, a method of imaging a radiographic image of a sample obtained as a result of the biopsy unit 70 collecting some tissue from the breast N of the examinee W) will be described using FIG. 7 to FIG. 16. The constituent elements of the radiographic imaging apparatus 10 are shown in FIG. 1 and FIG. 2.

Figure 7:
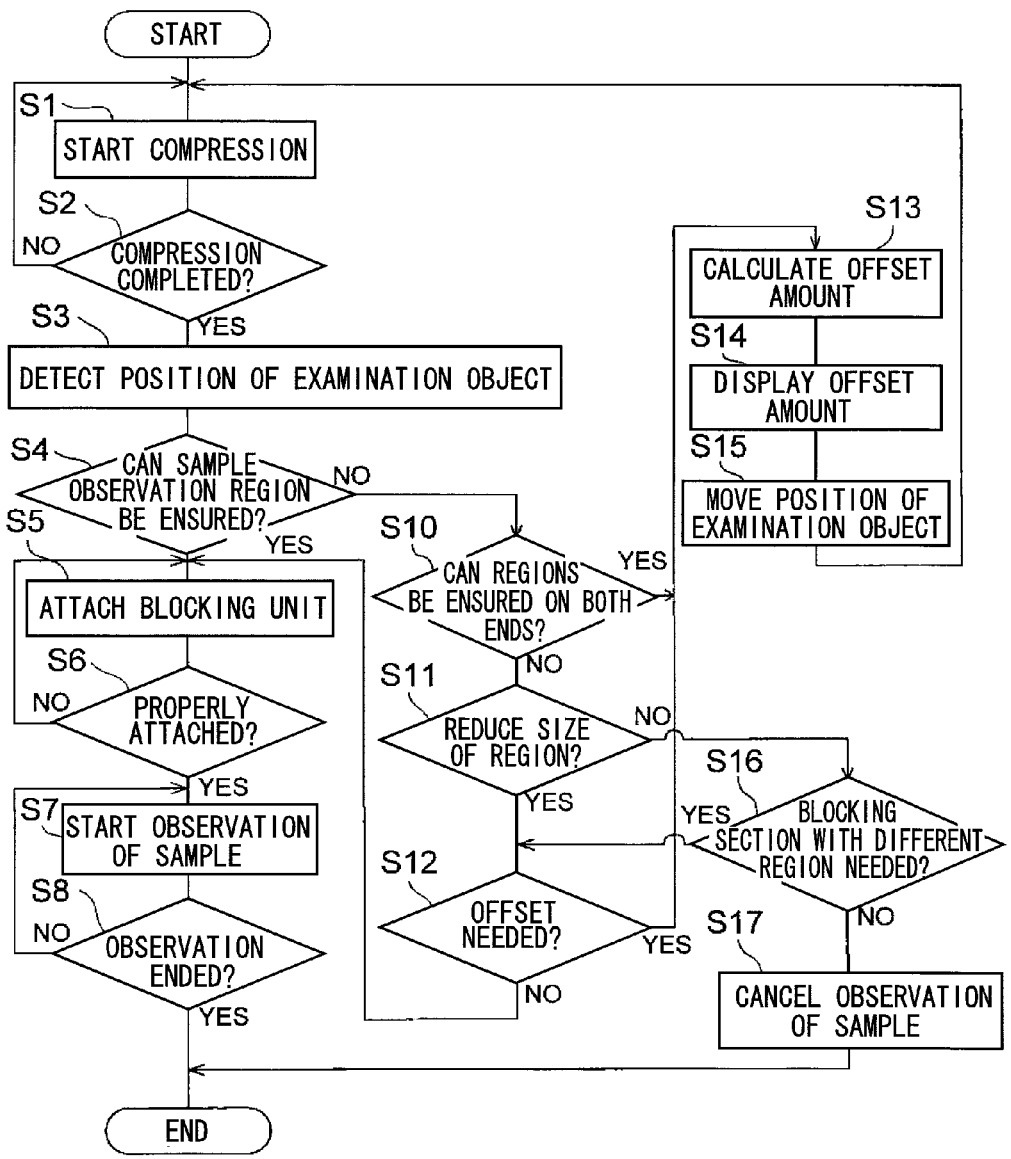
FIG. 7 is a flowchart describing a radiographic imaging method in the radiographic imaging apparatus according to the first exemplary embodiment.

As shown in FIG. 7, first, the breast N of the examinee W is placed on the object table surface 18 of the object table 16, and the breast N is squeezed and compressed between the object table surface 18 and the compression plate 22 (S1). Here, it is determined whether or not the compression of the breast N is complete (S2).

Next, the position including the shape of the outline of the breast N in the compressed state on the object table surface 18 is detected using the examination object position detection section 86 shown in FIG. 1 (S3). The technique for detecting the position of the breast N is not particularly limited. For example, the position of the breast N can be detected by exposing the breast N to a lower dose of the radiation R than the normal dose of the radiation R used in imaging, and using the radiation detector 20 to detect the radiation R that has been transmitted through the breast N. Furthermore, the position of the breast N can also be detected by using a marker disposed on the object table surface 18 as a reference and detecting whether or not the breast N is on the marker.

Figure 8:
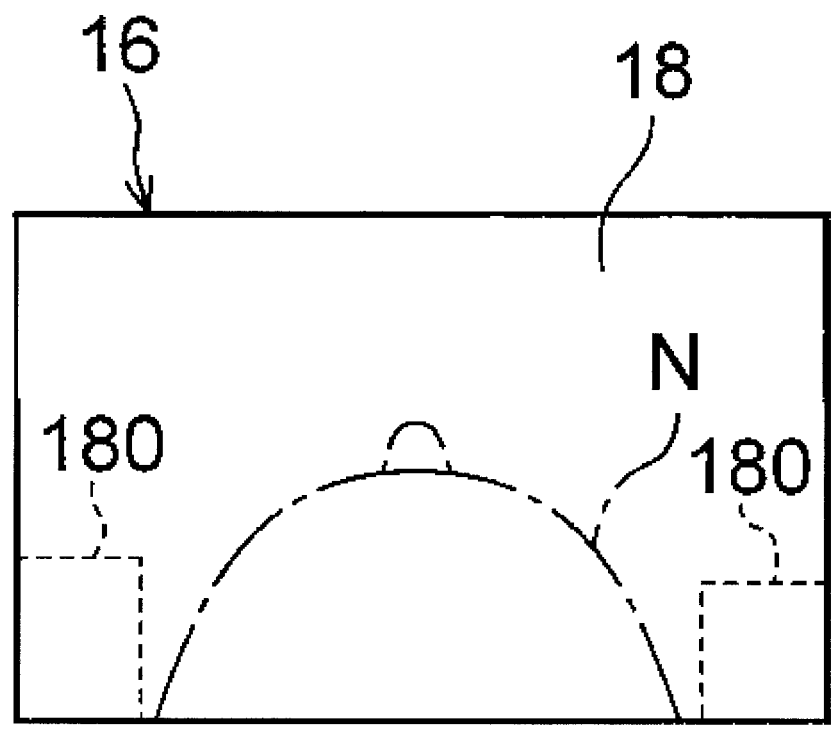
FIG. 8 is a schematic plan view of the object table surface showing the positional relationship between an examination object and observation regions (overlapping incidence regions) in the radiographic imaging method shown in FIG. 7.

On the basis of the detected position of the breast N, it is determined whether or not an observation region for the sample collected by the biopsy unit 70 can be ensured on the object table surface 18 (S4). It is determined that an observation region can be ensured if, as shown in FIG. 8, the breast N is in the central section of the object table surface 18 and there are empty spaces on the right-side outer peripheral portion and the left-side outer peripheral portion of the breast N—in other words, on the right and left end portions of the object table surface 18. The observation region corresponds to the overlapping incidence region 180 shown in FIG. 6 in which the incidence region 182 of the radiation R and the incidence region 184 of the visible light L overlap.

In a case where it has been determined that an observation region can be ensured, the radiation blocking unit 60 is attached between the radiation emitting section 12 and the object table surface 18 as shown in FIG. 1 and FIG. 3 to FIG. 5 (S5). Then, it is determined whether or not the radiation blocking unit 60 is properly attached (S6). In a case where the radiation blocking unit 60 is not properly attached, the radiation blocking unit 60 is reattached. Furthermore, in a case where the radiation blocking unit 60 is not properly attached, the operator is notified, by the notification section 88 shown in FIG. 1, that the radiation blocking unit 60 is not properly attached. The notification may be achieved by a warning sound or a warning indication displayed on an operation screen.

In a case where the radiation blocking unit 60 is properly attached, the sample is placed in the observation region (S7). Then, the sample is observed and a radiographic image of the sample is imaged. Here, when a radiographic image is to be imaged, the visible light L that has passed through the radiation blocking unit 60 from the visible light source 50 is emitted to the observation region (an end portion of the object table surface 18), and the incidence region of the visible light L is indicated as the incidence region of the radiation R. After the incidence region of the visible light L is determined as appropriate for the incidence region of the radiation R, the sample is exposed to the radiation R emitted from the radiation source 30 through the radiation blocking unit 60, and a radiographic image of the sample is imaged.

Figure 9A:
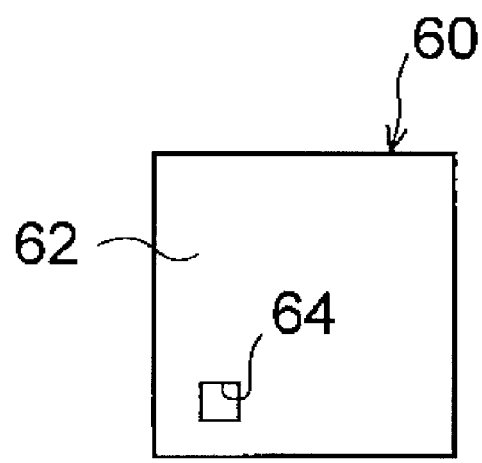
FIG. 9A is a schematic plan view showing, as seen from above, the top surface side of the radiation blocking unit used in the radiographic imaging method shown in FIG. 7.
Figure 9B:
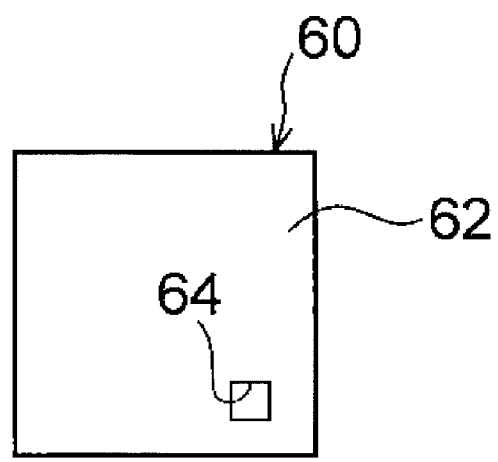
FIG. 9B is a schematic plan view showing, as seen from above, the bottom surface side of the radiation blocking unit shown in FIG. 9A.

Here, as shown in FIG. 3 to FIG. 5, the radiation blocking unit 60 of the radiographic imaging apparatus 10 according to the first exemplary embodiment has the through portions 64, the radiation blocking portions 66, and the visible light blocking portions 68 that are disposed as right and left pairs on the attachment member 62. For this reason, for example, in a case where the sample is placed only on the left-side end portion of the object table surface 18 and a radiographic image of the sample is to be imaged, the blocking plate 40 shown in FIG. 1 is moved so that the radiation R is emitted only to the left-side end portion of the object table surface 18. As shown in FIG. 9A, the attachment member 62 of the radiation blocking unit 60 may also be configured such that it has the through portion 64 (including the radiation blocking portion 66 and the visible light blocking portion 68) only on one side on the left end as seen from the top side. By reversing the top and bottom sides of the attachment member 62, the through portion 64 moves to the right end as shown in FIG. 9B. In this radiation blocking unit 60, the through portion 64 and so forth are disposed on either one of the right side and the left side, so the structure becomes simpler and manufacturing costs and so forth may be reduced.

When the observation and imaging of the sample ends (S8), the radiographic imaging method ends. In a case where it has been determined that the observation and imaging of the sample has not ended, the flow returns to step S7 and the observation and imaging of the sample is continued.

Figure 10:
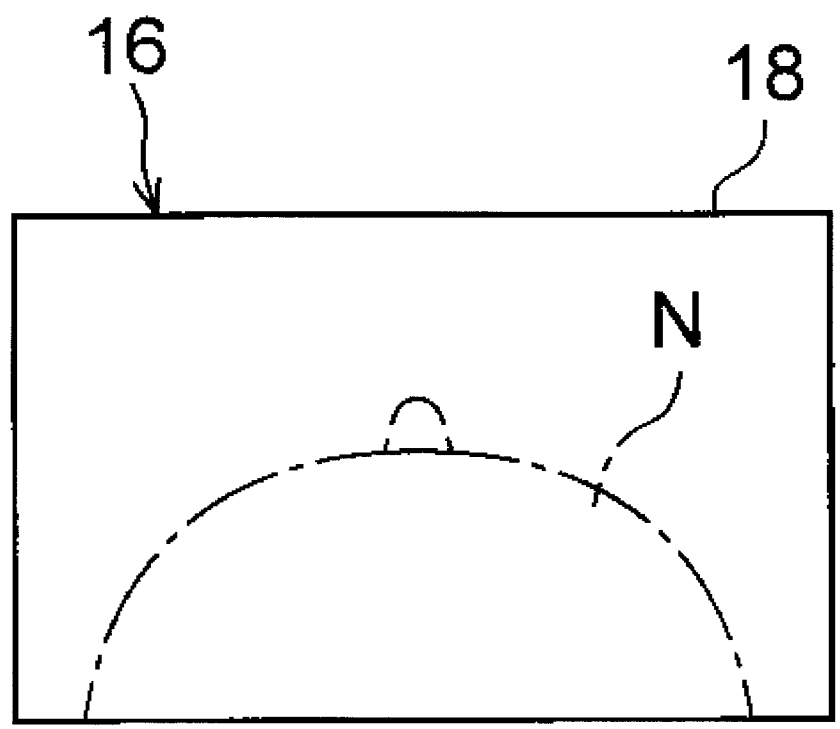
FIG. 10 is a schematic plan view of the object table surface corresponding to FIG. 8 showing the positional relationship between the object table surface and the examination object in the radiographic imaging method shown in FIG. 7.
Figure 11:
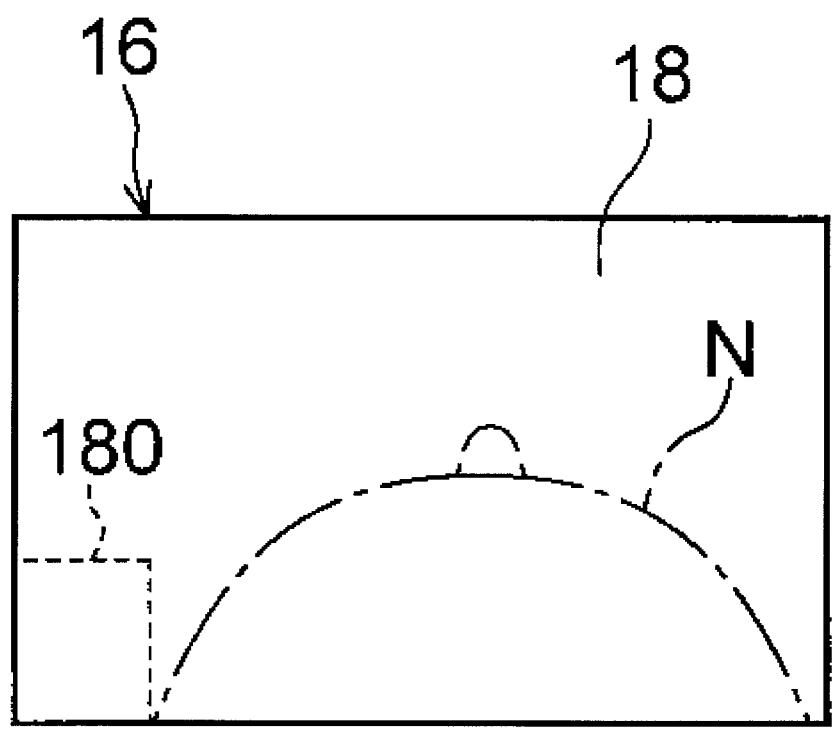
FIG. 11 is a schematic plan view of the object table surface corresponding to FIG. 8 showing the positional relationship between the examination object and the observation region in the radiographic imaging method shown in FIG. 7.
Figure 12:
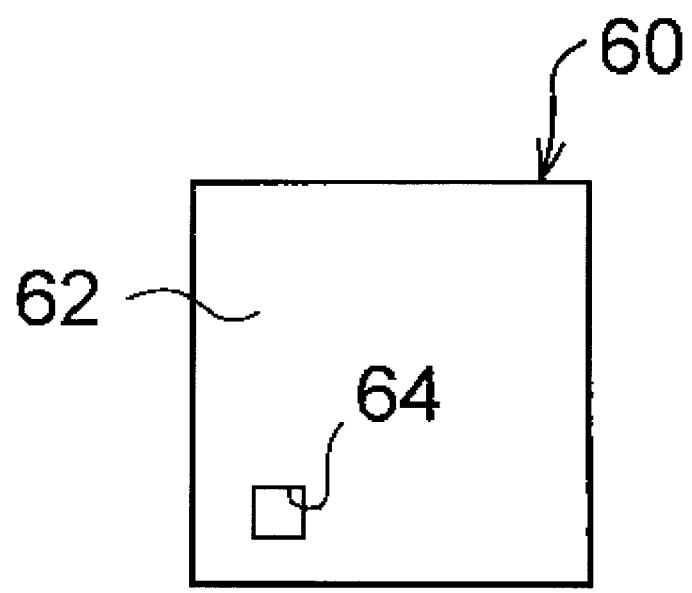
FIG. 12 is a schematic plan view showing, as seen from above, the top surface side of the radiation blocking unit used in the radiographic imaging method shown in FIG. 7.

In a case where, as shown in FIG. 10, the percentage of the area of the object table surface 18 occupied by the breast N is large and there is not much empty space on the right and left outer peripheral portions of the breast N, it is determined in step S4 that an observation region cannot be ensured. In this case, it is determined whether or not an observation region can be ensured if the positions of both the right and left ends of the breast N are adjusted relative to the object table surface 18 (S10). In a case where it has been determined that an observation region can be ensured, an offset amount of the breast N relative to the object table surface 18 is calculated from the information (mainly outline information) of the detected position of the breast N and information of the area needed for the observation region (S 13). The offset amount is displayed on the non-illustrated operation screen of the operation section 84 (S 14), and the position of the breast N is changed in accordance with the displayed offset amount (S15). For example, as shown in FIG. 11, by changing the position of the breast N to the right side, an observation region is ensured on the left-side outer periphery of the object table surface 18. At this time, as shown in FIG. 12, it suffices for the through portion 64 (also including the radiation blocking portion 66 and the visible light blocking portion 68) to be disposed on the left side of the attachment member 62 of the radiation blocking unit 60 as seen in a plan view.

Figure 13:
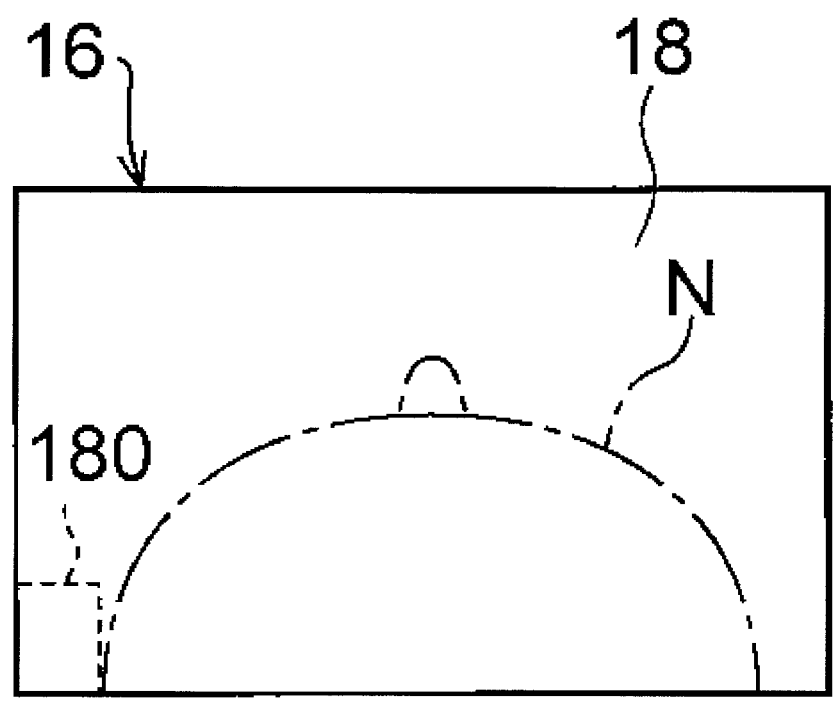
FIG. 13 is a schematic plan view of the object table surface corresponding to FIG. 8 showing the positional relationship between the examination object and the observation region in the radiographic imaging method shown in FIG. 7.
Figure 14:
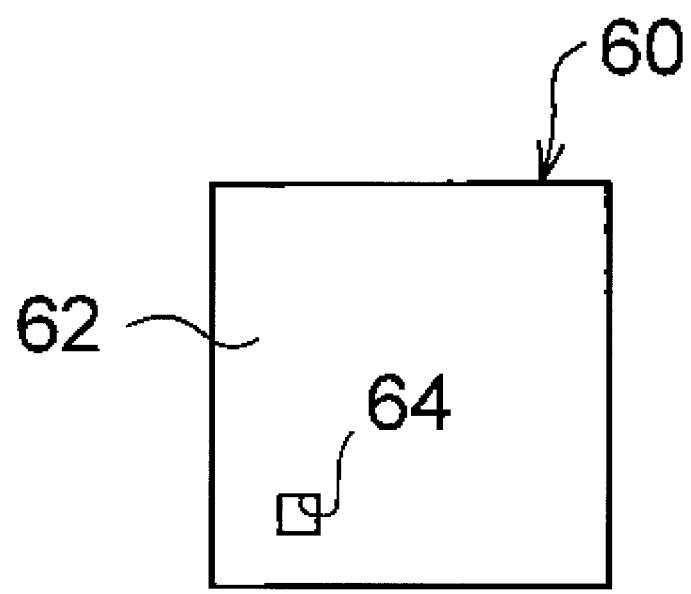
FIG. 14 is a schematic plan view showing, as seen from above, the top surface side of the radiation blocking unit used in the radiographic imaging method shown in FIG. 7.

In a case where it has been determined in step S10 that an observation region cannot be ensured, it is determined whether or not the size of the observation region (corresponding to the overlapping incidence region 180) can be reduced as shown in FIG. 13 (S11). In a case where it has been determined that the size of the observation region can be reduced, the open dimension of the through portion 64 disposed in the attachment member 62 of the radiation blocking unit 60 is reduced as shown in FIG. 14. Here, in the radiation blocking unit 60 according to the first exemplary embodiment, the position of the radiation blocking portion 66 can be adjusted using the position adjusting mechanisms 662 and 664 shown in FIG. 5, so that the open dimension of the through portion 64 can be reduced with respect to the radiation R. After this, it is determined whether or not an offset amount for adjusting the position of the breast N relative to the object table surface 18 is needed in accompaniment with the reduction in the size of observation region (S 12). In a case where it has been determined that an offset amount is needed, the processing of step S13 is executed. In a case where it has been determined that an offset amount is not needed, the processing of step S5 is executed.

Figure 15:
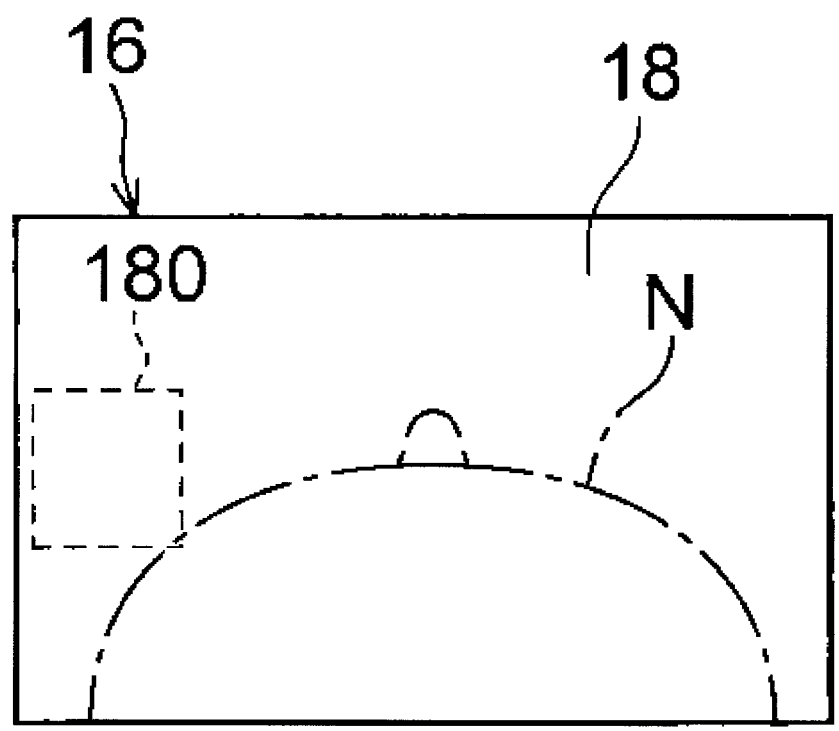
FIG. 15 is a schematic plan view of the object table surface corresponding to FIG. 8 showing the positional relationship between the examination object and the observation region in the radiographic imaging method shown in FIG. 7.
Figure 16:
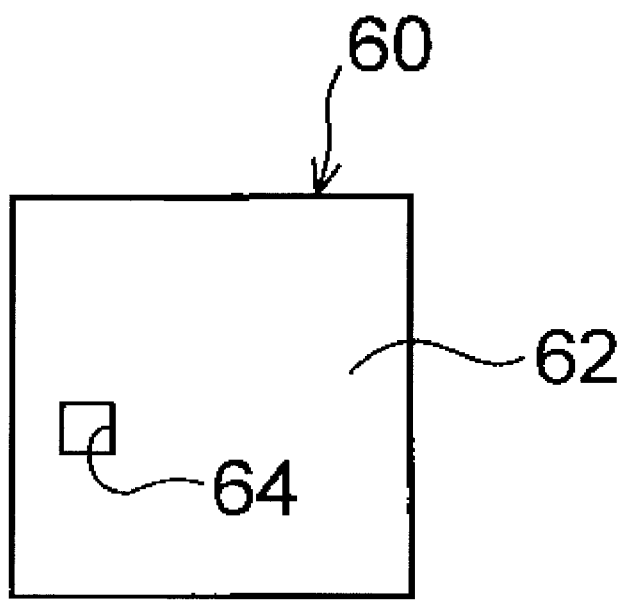
FIG. 16 is a schematic plan view showing, as seen from above, the top surface side of the radiation blocking unit used in the radiographic imaging method shown in FIG. 7.

In a case where it has been determined in step S11 that an observation region cannot be ensured by reducing the size of the observation region, it is determined whether or not a radiation blocking unit 60 with a different observation region, in which the observation region (corresponding to the overlapping incidence region 180) is moved toward the back side, is needed as shown in FIG. 15 (S16). In a case where it has been determined that a radiation blocking unit 60 with a different observation region is needed, a radiation blocking unit 60 having an attachment member 62 in which the position of the through portion 64 is moved toward the back side is selected as shown in FIG. 16, and the processing of step S12 is executed. In a case where it has been determined that a radiation blocking unit 60 with a different observation region is not needed, the observation of the sample is cancelled (S 17) and the radiographic imaging method ends.

As described above, in the radiation blocking unit 60 according to the first exemplary embodiment, as shown in FIG. 1 and FIG. 3 to FIG. 5, the attachment member 62 is attachable between the sources 30 and 50 and the object table surface 18, and the radiation blocking portion 66 and the visible light blocking portion 68 are disposed on the attachment member 62. Here, as shown in FIG. 6, the radiation blocking portion 66 transmits the visible light L emitted to the overlapping incidence region 180 on the object table surface 18 in which the incidence region 182 of the radiation R and the incidence region 184 of the visible light L overlap, and blocks the radiation irradiated outside the overlapping incidence region 180. The visible light blocking portion 68 transmits the radiation R emitted to the overlapping incidence region 180, and blocks the visible light L emitted outside the overlapping incidence region 180. For this reason, the radiation R and the visible light L emitted outside the overlapping incidence region 180 are blocked, so only the radiation R and the visible light L emitted to the overlapping incidence region 180 are transmitted to the object table surface 18.

Consequently, according to the radiation blocking unit 60 according to the first exemplary embodiment, the precision with which the incidence region 182, on the object table surface 18, of the radiation R emitted from the radiation source 30 and the incidence region 184, on the object table surface 18, of the visible light L emitted from the visible light source 50 coincide may be improved.

Furthermore, in the radiation blocking unit 60 according to the first exemplary embodiment, the precision with which the incidence region 182 of the radiation R emitted to the object table surface 18 outside the boundary of the breast N serving as the examination object and the incidence region 184 of the visible light L coincide is improved. For this reason, a radiographic image may be imaged outside the boundary of the breast N in a state in which the breast N is on the object table surface 18.

Moreover, in the radiation blocking unit 60 according to the first exemplary embodiment, as shown in FIG. 5, the attachment member 62 is configured by a plate having the through portion 64, and the radiation blocking portion 66 is disposed on this plate via the position adjusting mechanisms 662 and 664. Here, the position adjusting mechanisms 662 and 664 can adjust the position of the radiation blocking portion 66 in the planar direction of the plate. For this reason, the position of the incidence region 182 of the radiation R emitted outside the overlapping incidence region 180 can be adjusted by the position adjusting mechanisms 182 and 184, so the precision with which the incidence region 182 of the radiation R and the incidence region 184 of the visible light L coincide may be improved even more.

Furthermore, in the radiation blocking unit 60 according to the first exemplary embodiment, the plate configuring the attachment member 62 can be used as a blocking portion that blocks the radiation R and the visible light L. For this reason, the configuration that moves the incidence regions of the radiation R and the visible light L may be simplified. For example, the configuration of the blocking plate 40 moving mechanism for moving and changing the incidence region of the radiation R inside the collimator box 14 may be simplified.

Moreover, in the radiation blocking unit 60 according to the first exemplary embodiment, the plate configuring the attachment member 62 is formed of a rolled steel plate, and the radiation R from the radiation source 30 and the visible light L from the visible light source 50 are blocked by the rolled steel plate. For this reason, the configuration that moves the incidence regions of the radiation R and the visible light L inside the collimator box 14 may be simplified. Furthermore, because the rolled steel plate is a general-purpose material, the radiation blocking unit 60 may be easily manufactured and manufacturing costs may be reduced.

Furthermore, in the radiation blocking unit 60 according to the first exemplary embodiment, the radiation blocking portion 66 is formed of lead glass and the visible light blocking portion 68 is formed of carbon-glass fiber. For this reason, the radiation blocking unit 60 can be easily manufactured because lead glass and carbon-glass fiber are both general-purpose materials.

Moreover, in the radiographic imaging apparatus 10 according to the first exemplary embodiment, as shown in FIG. 1, the visible light L from the visible light source 50 is emitted to the object table surface 18 of the object table 16 by the visible light illumination control section 52 serving as visible light emitting section, and the incidence region of the radiation R is indicated by the incidence region of the visible light L. The radiation irradiation control section 32 serving as radiation emitting section controls the emission of the radiation R from the radiation source 30, and the radiation R from the radiation source 30 is emitted to the object table surface 18 through the blocking plate 40. The blocking plate 40 can be moved, by the blocking plate drive section 42 serving as blocking plate moving section, in a direction intersecting the direction in which the radiation R is emitted, and when the blocking plate 40 moves, the incidence region 182 of the radiation R on the object table surface 18 moves.

Here, the radiation blocking portion 66 and the visible light blocking portion 68 are disposed between the object table surface 18 and the blocking plate 40. The radiation blocking portion 66 transmits the visible light L emitted to the overlapping incidence region 180 on the object table surface 18 in which the incidence region 182 of the radiation R and the incidence region 184 of the visible light L overlap and blocks the radiation R emitted outside the overlapping incidence region 180. The visible light blocking portion 68 transmits the radiation R emitted to the overlapping incidence region 180 and blocks the visible light L emitted outside the overlapping incidence region 180. For this reason, the radiation R and the visible light L emitted outside the overlapping incidence region 180 are blocked, so only the radiation R and the visible light L emitted to the overlapping incidence region 180 are transmitted to the object table surface 18. Consequently, even if the incidence region 182 of the radiation R is moved in accompaniment with the movement of the blocking plate 40, the incidence region 182 of the radiation R and the incidence region 184 of the visible light L coincide.

Furthermore, in the radiographic imaging apparatus 10 according to the first exemplary embodiment, the biopsy unit 70 is disposed between the object table surface 18 and the blocking plate 40. For this reason, tissue can be examined by the biopsy unit 70. For example, the radiographic imaging apparatus 10 can use the biopsy unit 70 to capture a radiographic image of tissue outside the boundary of the breast N serving as the examination object in a state in which the breast N is on the object table surface 18.

Moreover, in the radiographic imaging apparatus 10 according to the first exemplary embodiment, the compression plate 22 is disposed between the object table 16 and the blocking plate 40, and the compression plate 22 can compress the breast N serving as the examination object. That is, the radiographic imaging apparatus 10 may be applied to a mammography machine.

Furthermore, in the radiographic imaging method according to the first exemplary embodiment, when the position of the breast N serving as the examination object on the object table surface 18 is detected, the tissue observation region is set outside the boundary of the breast N on the object table surface 18 on the basis of the position of the breast N. The visible light L indicating the incidence region 182 of the radiation R is emitted from the visible light source 50 to the observation region, and then the radiation R is emitted to the observation region. The radiographic image of the tissue is generated on the basis of the radiation R that has been emitted to the observation region (corresponding to the overlapping incidence region 180).

Here, the visible light L emitted outside the observation region is blocked, and the radiation R emitted outside the observation region is blocked. For this reason, the visible light L and the radiation R are emitted only to the observation region, so the incidence region 184 of the visible light L and the incidence region 182 of the radiation R coincide.

[Second Exemplary Embodiment]

A second exemplary embodiment of the present invention will be described using FIG. 17 to FIG. 25. The second embodiment describes example modifications of the radiation blocking unit 60 and the radiographic imaging apparatus 10 according to the first exemplary embodiment.

EXAMPLE 1

Figure 17:
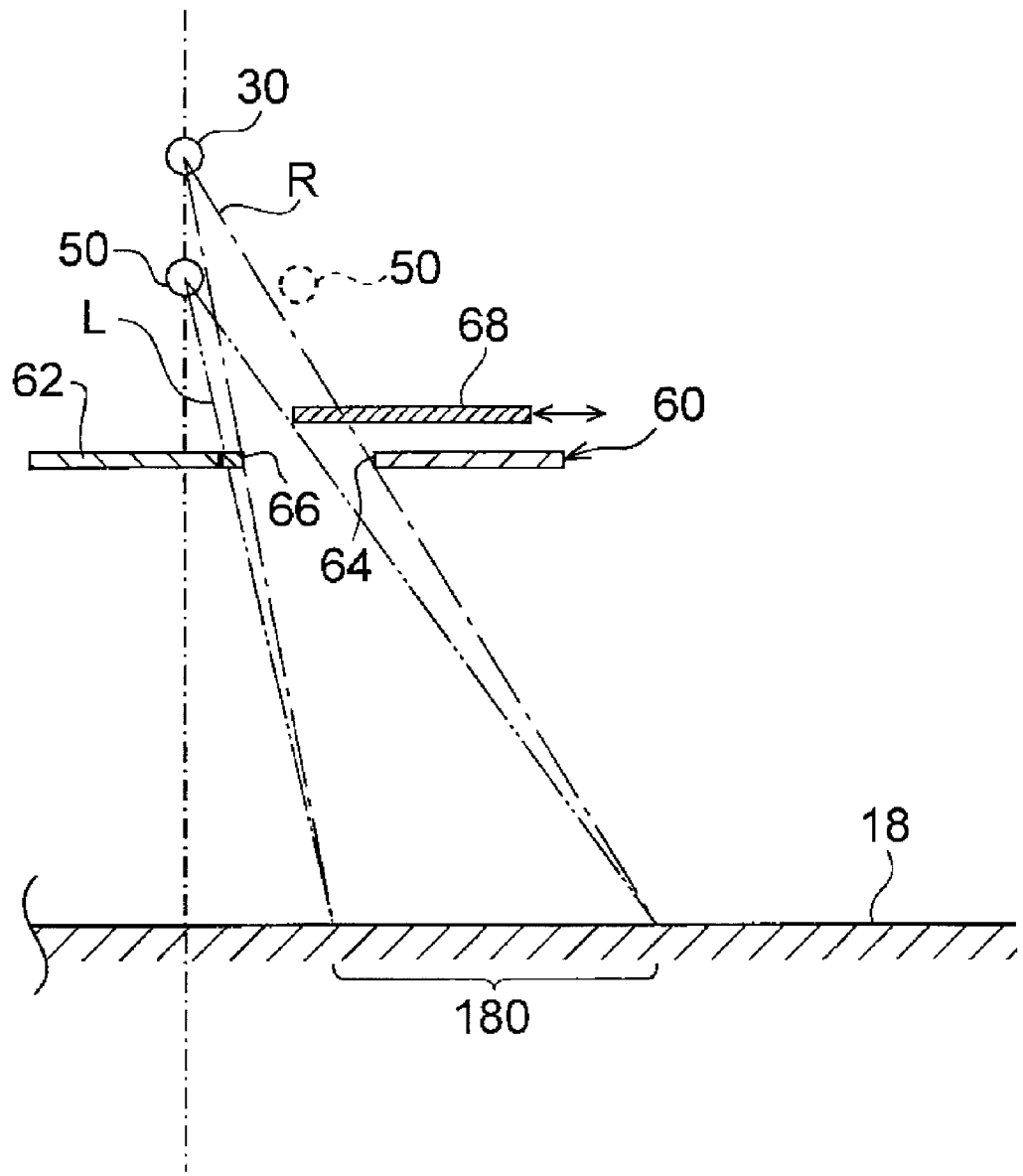
FIG. 17 is a schematic configuration diagram of the radiation blocking unit and the radiographic imaging apparatus according to example 1 of a second exemplary embodiment of the present invention.

As shown in FIG. 17, in the radiographic imaging apparatus 10 according to example 1 of the second exemplary embodiment, the visible light source 50 and the radiation source 30 are sequentially disposed heading upward from the object table surface 18 in a direction perpendicular to the object table surface 18. The radiation blocking portion 66 is fixed to the attachment member 62 of the radiation blocking unit 60. Furthermore, the visible light blocking portion 68 is attached to the attachment member 62, and position adjusting mechanisms that are the same as the position adjusting mechanisms 662 and 664 shown in FIG. 5 are disposed for the visible light blocking portion 68. In other words, the position of the visible light blocking portion 68 can be adjusted. The visible light blocking portion 68 may also be disposed in the collimator box 14 shown in FIG. 1 rather than being disposed in the radiation blocking unit 60. In this case, it is preferred that the visible light blocking portion 68 be movable like the blocking plate 40.

In the radiation blocking unit 60 and the radiographic imaging apparatus 10 according to example 1, the position adjusting mechanisms are switched from the radiation blocking portion 66 to the visible light blocking portion 68, and the same action and effects as those obtained by the radiation blocking unit 60 and the radiographic imaging apparatus 10 according to the first exemplary embodiment may be obtained. In example 1, the visible light source 50 is disposed directly under the radiation source 30, but the visible light source 50 may also be disposed in a position offset in the horizontal direction relative to the radiation source 30 as indicated by the dashed line.

EXAMPLE 2

Figure 18:
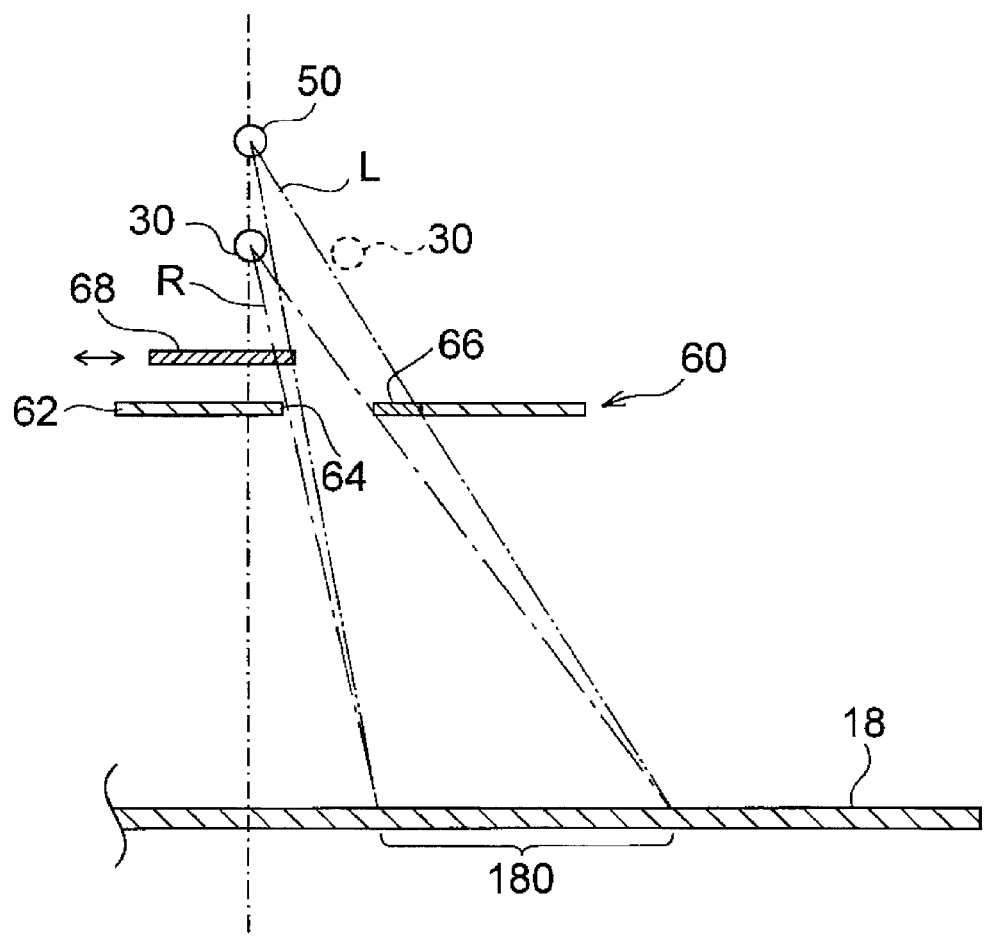
FIG. 18 is a schematic configuration diagram of the radiation blocking unit and the radiographic imaging apparatus according to example 2.

As shown in FIG. 18, in the radiographic imaging apparatus 10 according to example 2, the positional relationship between the visible light source 50 and the radiation source 30 in the up and down direction is reversed, and other configurations are the same as those in the radiographic imaging apparatus 10 according to example 1. Furthermore, the configuration of the radiation blocking unit 60 is the same as the configuration of the radiation blocking unit 60 according to example 1 except that the positional relationship between the radiation blocking portion 66 and the visible light blocking portion 68 is reversed.

In the radiation blocking unit 60 and the radiographic imaging apparatus 10 according to example 2, the same action and effects as those obtained by the radiation blocking unit 60 and the radiographic imaging apparatus 10 according to the first exemplary embodiment are obtained. Furthermore, in example 2, the radiation source 30 is disposed directly under the visible light source 50, but like in the first example, the radiation source 30 may also be disposed in a position offset in the horizontal direction relative to the visible light source 50 as indicated by the dashed line.

EXAMPLE 3

Figure 19:
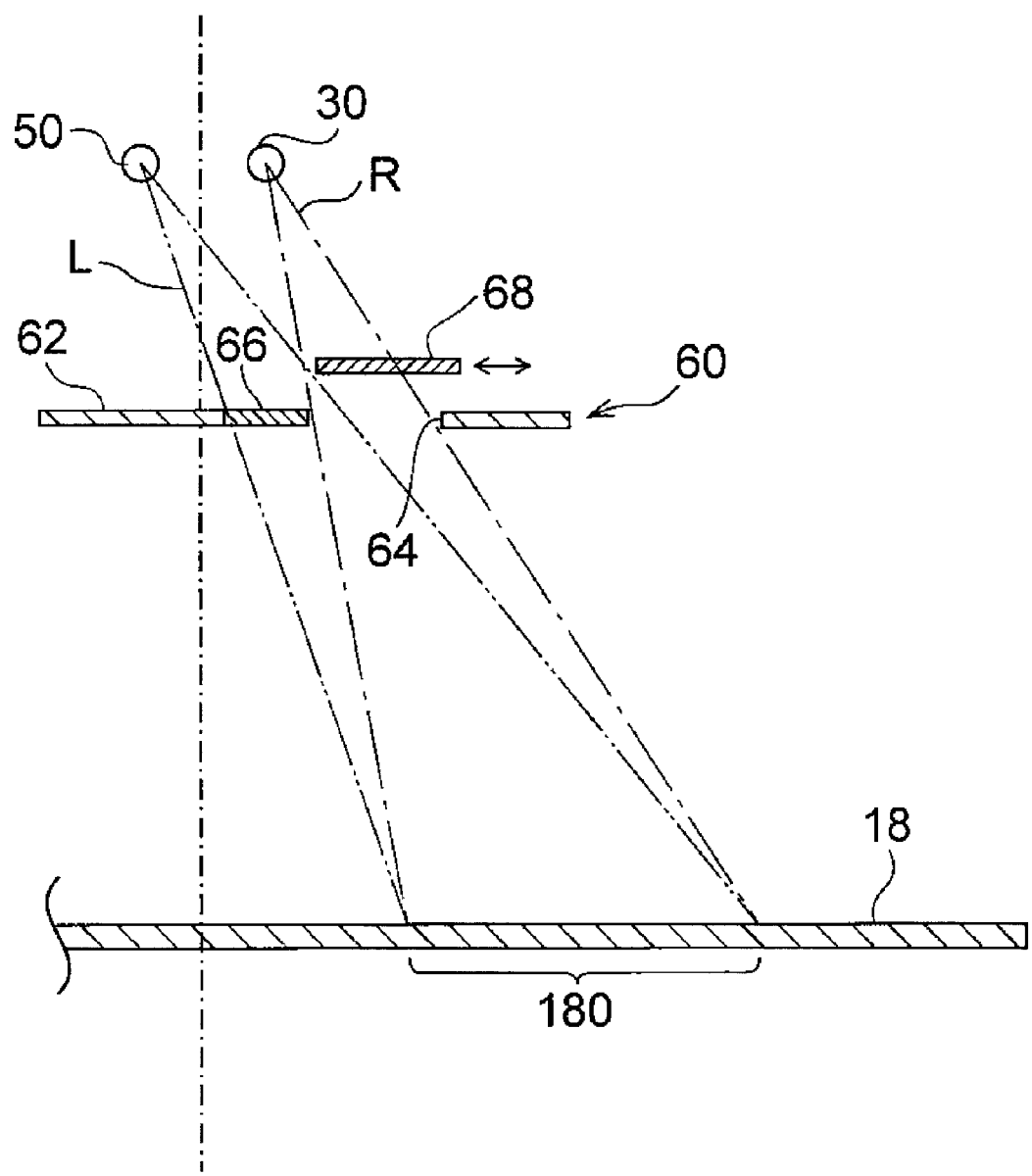
FIG. 19 is a schematic configuration diagram of the radiation blocking unit and the radiographic imaging apparatus according to example 3.

As shown in FIG. 19, in the radiographic imaging apparatus 10 according to example 3, the distances of the radiation source 30 and the visible light source 50 from the object table surface 18 are set equal to one another, and the radiation source 30 and the visible light source 50 are spaced apart from one another in the horizontal direction. Other configurations are the same as those in the radiographic imaging apparatus 10 according to example 1. The configuration of the radiation blocking unit 60 is the same as the configuration of the radiation blocking unit 60 according to example 1.

In the radiation blocking unit 60 and the radiographic imaging apparatus 10 according to example 3, the same action and effects as those obtained by the radiation blocking unit 60 and the radiographic imaging apparatus 10 according to example 1 are obtained.

EXAMPLE 4

Figure 20:
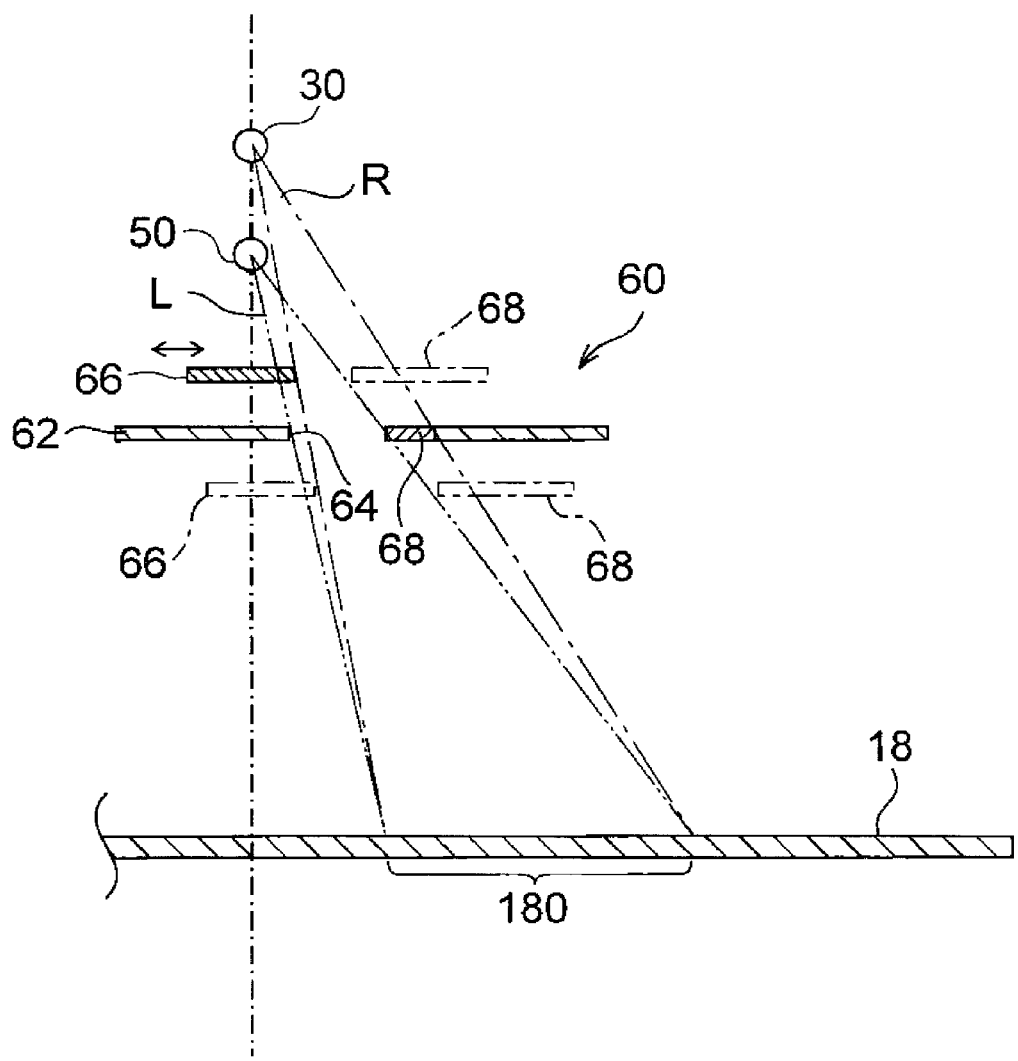
FIG. 20 is a schematic configuration diagram of the radiation blocking unit and the radiographic imaging apparatus according to example 4.

As shown in FIG. 20, in the radiographic imaging apparatus 10 according to example 4, the positional relationship between the visible light source 50 and the radiation source 30 is the same as the positional relationship between the visible light source 50 and the radiation source 30 in the radiographic imaging apparatus 10 according to example 1. The radiation blocking unit 60 has a configuration that is the same as the configuration of the radiation blocking unit 60 according to the first exemplary embodiment. That is, the radiation blocking unit 60 takes as main components and is configured by the radiation blocking portion 66, which is disposed on the attachment member 62 and whose position can be adjusted by the non-illustrated position adjusting mechanisms 662 and 664, and the visible light blocking portion 68, which is fixed to the attachment member 62.

In the radiation blocking unit 60 according to example 4, the radiation blocking portion 66 is disposed on the top surface side of the attachment member 62, but the radiation blocking portion 66 may also be disposed on the bottom surface side of the attachment member 62 as indicated by the long dashed short dashed line. Furthermore, the visible light blocking portion 68 may also be disposed on the top surface side or the bottom surface side of the attachment member 62 as indicated by the long dashed short dashed lines, and the position of the visible light blocking portion 68 in this case can be changed by position adjusting mechanisms that are the same as the position adjusting mechanisms 662 and 664. Moreover, in example 4 and also in example 5 and example 6 described below, rather than disposing the radiation blocking portion 66 in the radiation blocking unit 60, the blocking plate 40 in the collimator box 14 shown in FIG. 1 may also double as the radiation blocking portion 66.

In the radiation blocking unit 60 and the radiographic imaging apparatus 10 according to example 4, the same action and effects as those obtained by the radiation blocking unit 60 and the radiographic imaging apparatus 10 according to the first exemplary embodiment can be obtained.

Furthermore, in the radiation blocking unit 60 according to example 4, the attachment member 62 is configured by a plate having the through portion 64, and both the radiation blocking portion 66 and the visible light blocking portion 68 are disposed on this plate via the position adjusting mechanisms 662 and 664 shown in FIG. 5. Here, the position adjusting mechanisms 662 and 664 can adjust the positions of both the radiation blocking portion 66 and the visible light blocking portion 68 in the planar direction of the plate. For this reason, the positions of the incidence regions 182 and 184 of the radiation R and the visible light L emitted outside the overlapping incidence region 180 can be adjusted by the position adjusting mechanisms 662 and 664, so the precision with which the incidence region 182 of the radiation R and the incidence region 184 of the visible light L coincide may be further improved.

EXAMPLE 5

Figure 21:
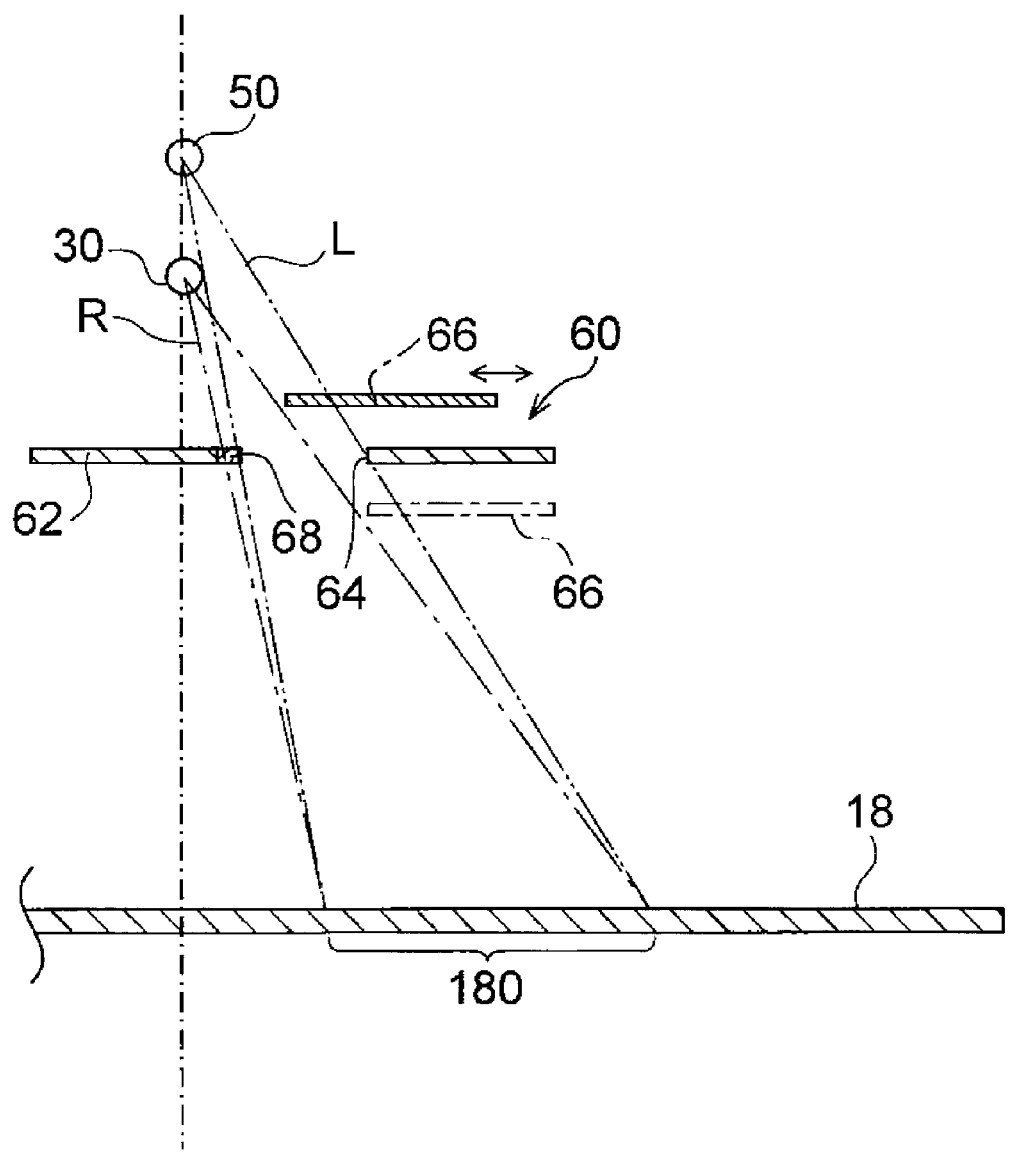
FIG. 21 is a schematic configuration diagram of the radiation blocking unit and the radiographic imaging apparatus according to example 5.

As shown in FIG. 21, in the radiographic imaging apparatus 10 according to example 5, the positional relationship between the visible light source 50 and the radiation source 30 in the up and down direction is reversed, and other configurations are the same as those in the radiographic imaging apparatus 10 according to example 4. Furthermore, the configuration of the radiation blocking unit 60 is the same as the configuration of the radiation blocking unit 60 according to example 4 except that the positional relationship between the radiation blocking portion 66 and the visible light blocking portion 68 is reversed.

In the radiation blocking unit 60 and the radiographic imaging apparatus 10 according to example 5, the same action and effects as those obtained by the radiation blocking unit 60 and the radiographic imaging apparatus 10 according to example 4 may be obtained.

EXAMPLE 6

Figure 22:
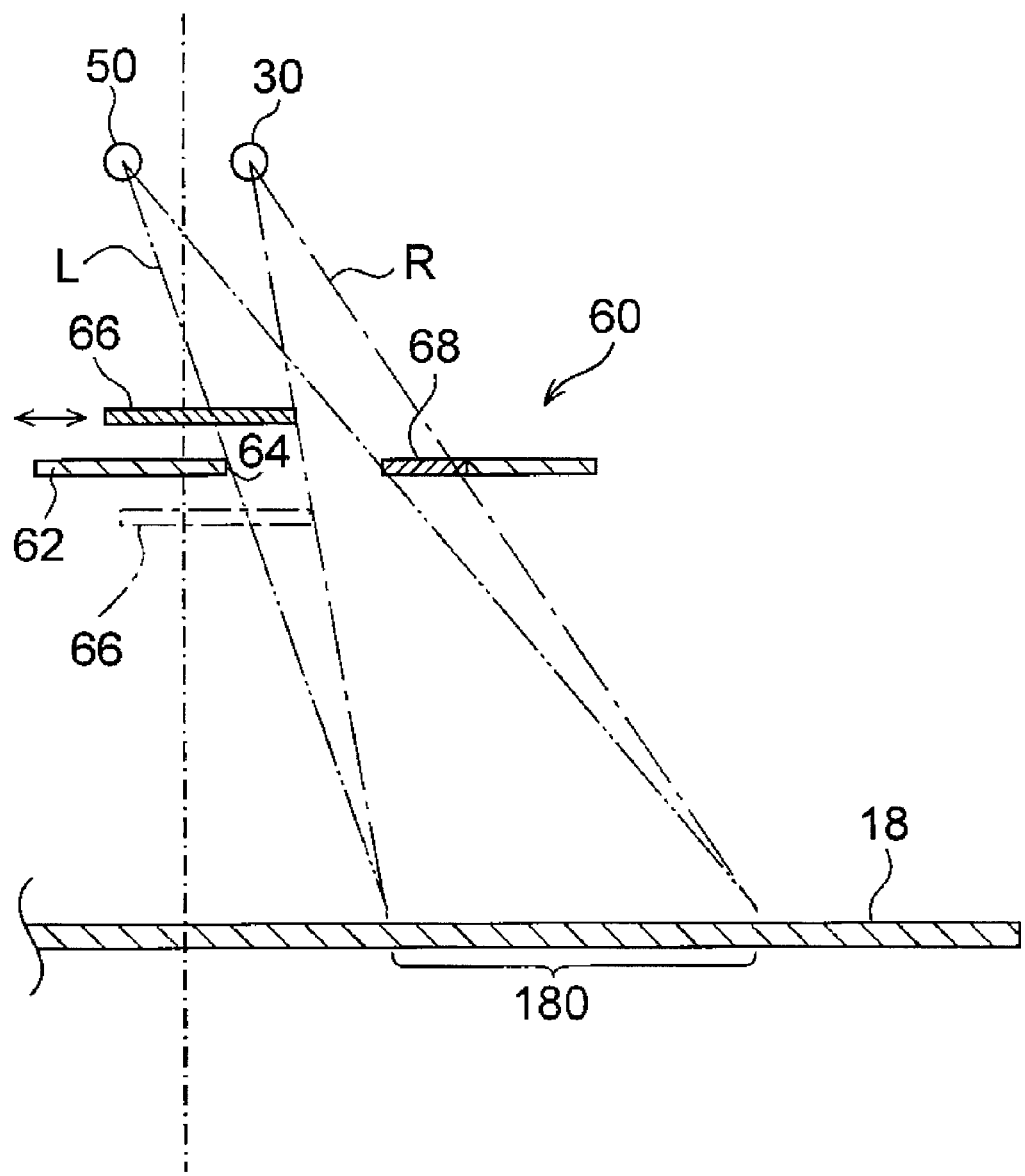
FIG. 22 is a schematic configuration diagram of the radiation blocking unit and the radiographic imaging apparatus according to example 6.

As shown in FIG. 22, in the radiographic imaging apparatus 10 according to example 6, the radiation source 30 and the visible light source 50 are set at equal heights from the object table surface 18 like in the radiographic imaging apparatus 10 according to example 3. Other configurations are the same as those in the radiographic imaging apparatus 10 according to example 4. Consequently, the configuration of the radiation blocking unit 60 is the same as the configuration of the radiation blocking unit 60 according to example 4.

In the radiation blocking unit 60 and the radiographic imaging apparatus 10 according to example 6, the same action and effects as those obtained by the radiation blocking unit 60 and the radiographic imaging apparatus 10 according to example 4 may be obtained.

EXAMPLE 7

Figure 23:
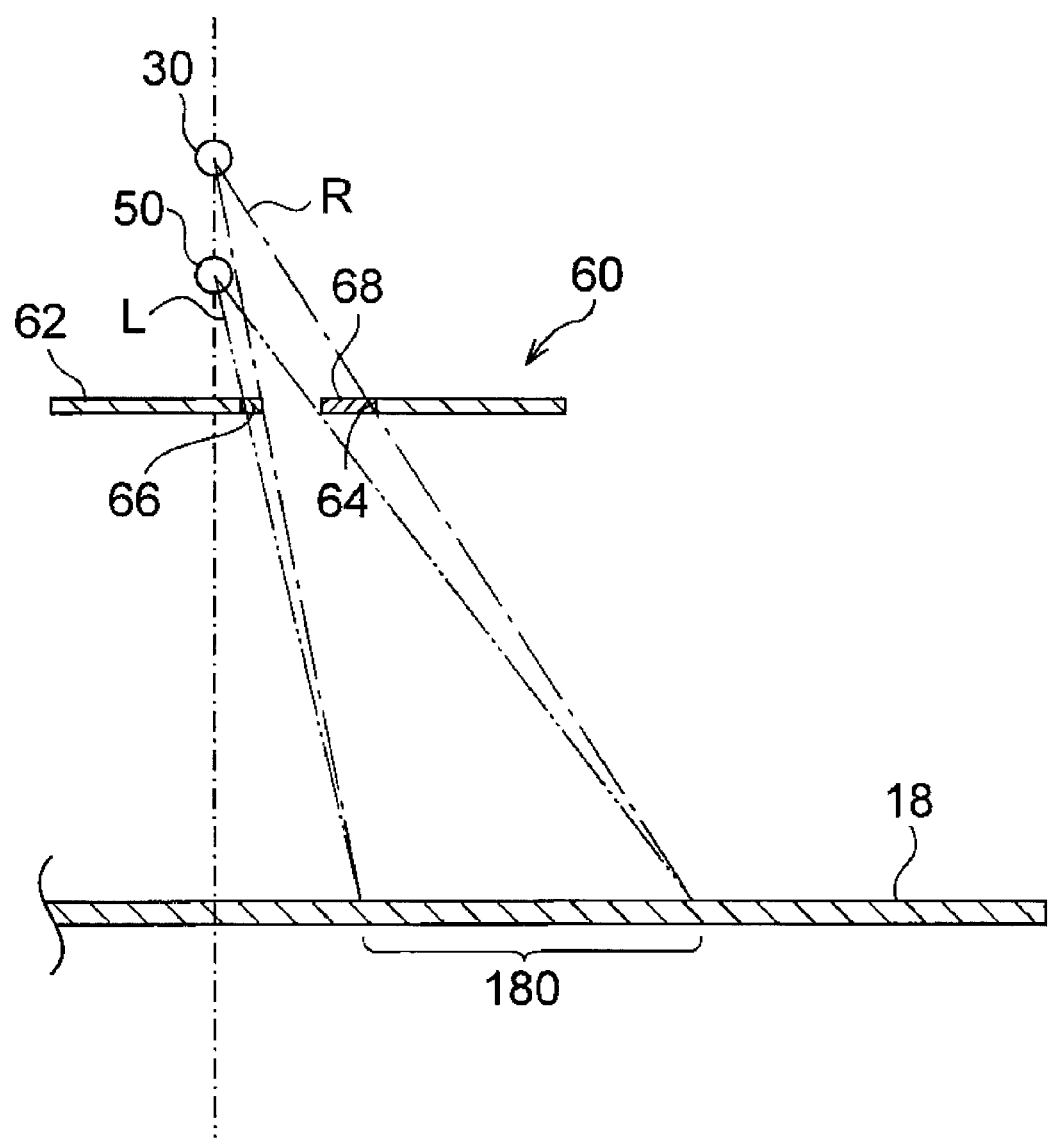
FIG. 23 is a schematic configuration diagram of the radiation blocking unit and the radiographic imaging apparatus according to example 7.

As shown in FIG. 23, in the radiographic imaging apparatus 10 according to example 7, the positional relationship between the visible light source 50 and the radiation source 30 is the same as the positional relationship between the visible light source 50 and the radiation source 30 in the radiographic imaging apparatus 10 according to example 1. The radiation blocking unit 60 takes as main components and is configured by the radiation blocking portion 66, which is fixed to the attachment member 62 without the position adjusting mechanisms 662 and 664 being disposed, and the visible light blocking portion 68, which is likewise fixed to the attachment member 62.

In the radiation blocking unit 60 and the radiographic imaging apparatus 10 according to example 7, the same action and effects as those obtained by the radiation blocking unit 60 and the radiographic imaging apparatus 10 according to example 4 may be obtained. Furthermore, in the radiation blocking unit 60, the radiation blocking portion 66 and the visible light portion 68 are simply fixed to the attachment member 62, so the structure may be simplified.

EXAMPLE 8

Figure 24:
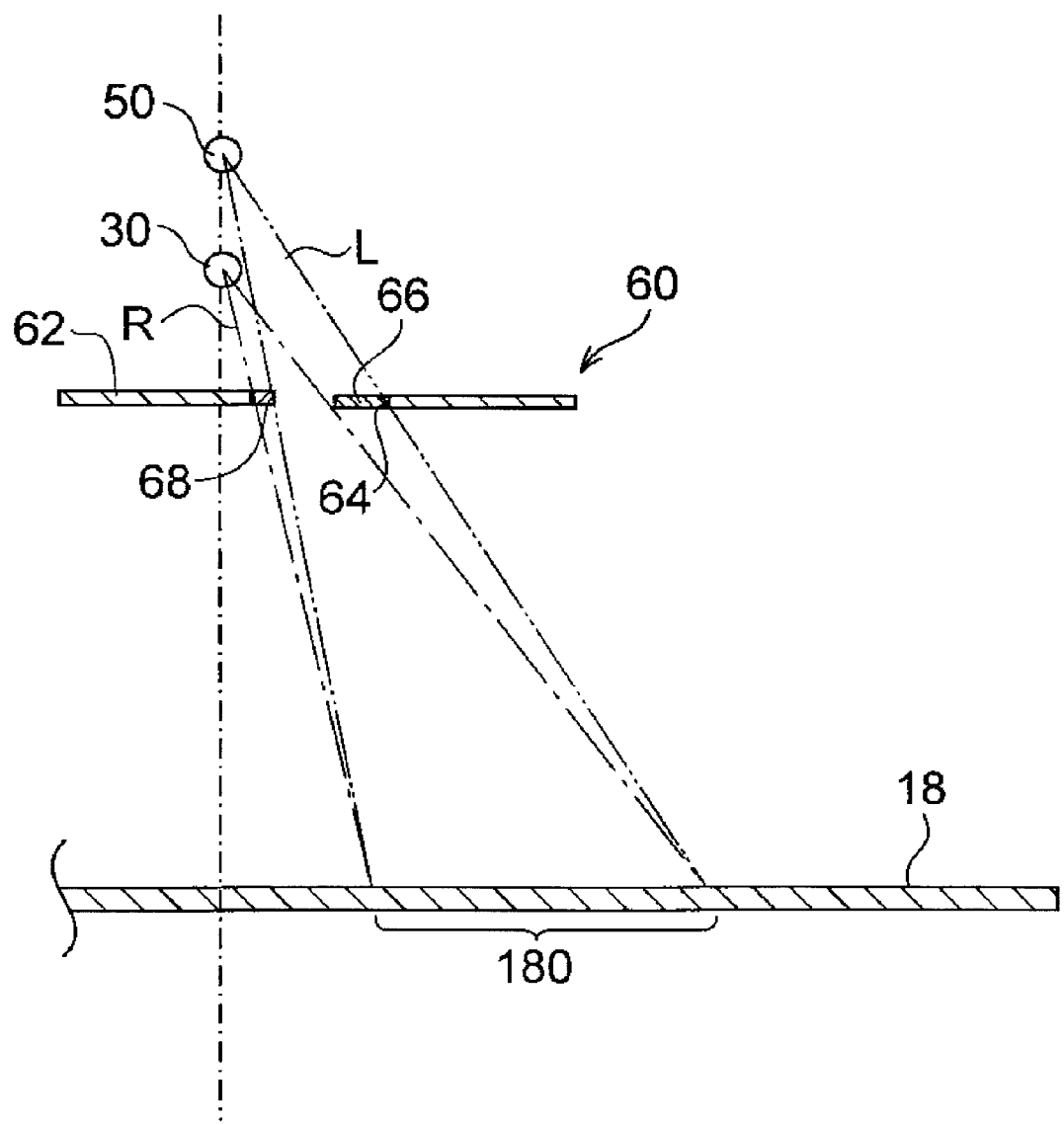
FIG. 24 is a schematic configuration diagram of the radiation blocking unit and the radiographic imaging apparatus according to example 8.

As shown in FIG. 24, in the radiographic imaging apparatus 10 according to example 8, the positional relationship between the visible light source 50 and the radiation source 30 in the up and down direction is reversed, and other configurations are the same as those in the radiographic imaging apparatus 10 according to example 7. Furthermore, the configuration of the radiation blocking unit 60 is the same as the configuration of the radiation blocking unit 60 according to example 7 except that the positional relationship between the radiation blocking portion 66 and the visible light blocking portion 68 is reversed.

In the radiation blocking unit 60 and the radiographic imaging apparatus 10 according to example 8, the same action and effects as those obtained by the radiation blocking unit 60 and the radiographic imaging apparatus 10 according to example 7 may be obtained.

EXAMPLE 9

Figure 25:
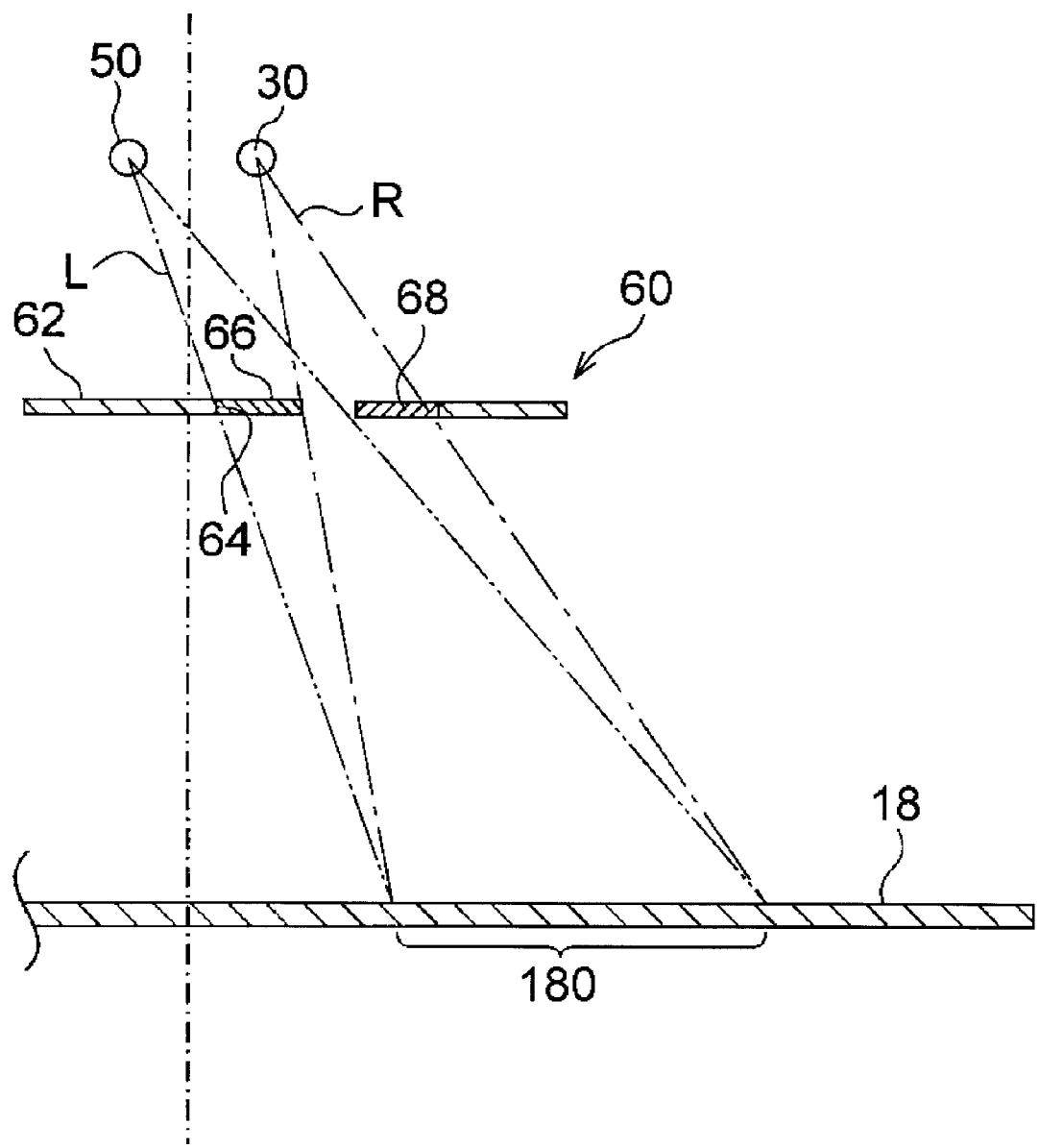
FIG. 25 is a schematic configuration diagram of the radiation blocking unit and the radiographic imaging apparatus according to example 9.

As shown in FIG. 25, in the radiographic imaging apparatus 10 according to example 9, the radiation source 30 and the visible light source 50 are set at equal heights from the object table surface 18 like in the radiographic imaging apparatus 10 according to example 3. Other configurations are the same as those in the radiographic imaging apparatus 10 according to example 7. Consequently, the configuration of the radiation blocking unit 60 is the same as the configuration of the radiation blocking unit 60 according to example 7.

In the radiation blocking unit 60 and the radiographic imaging apparatus 10 according to example 9, the same action and effects as those obtained by the radiation blocking unit 60 and the radiographic imaging apparatus 10 according to example 7 may be obtained.

[Alternative Exemplary Embodiments]

The present invention has been described above using several exemplary embodiments and several examples, but the present invention is not limited to these exemplary embodiments and can be changed in a variety of ways without departing from the gist thereof. For example, the present invention is not limited to a mammography machine and is widely applicable to radiographic imaging apparatus having the function of using visible light from a visible light source to indicate a incidence region of radiation from a radiation source.

What is claimed is:

1. A radiation blocking unit for use with a radiographic imaging system that includes a radiation source, a visible light source, a radiation emitting section including a collimator box having a radiation-blocking plate that defines an incidence region of radiation irradiated from the radiation source and an optical mirror that coincides visible light illuminated from the visible light source with the incidence region of the radiation, and an object table surface to which the radiation and the visible light are emitted, the radiation blocking unit comprising:

an attachment member that is detachably attachable between the radiation emitting section and the visible light source, and the object table surface, the attachment member being made of a material, and having a thickness, such that the attachment member transmits nether radiation, nor visible light, the attachment member having one or more through portions that define an incidence region of the radiation and an incidence region of the visible light on the object table surface;

a radiation blocking portion, disposed on the attachment member via a position adjusting mechanism that adjusts a position of the radiation blocking portion, the radiation blocking portion transmitting the illuminated visible light and blocking the irradiated radiation; and a visible light blocking portion, disposed on the attachment member via a position adjusting mechanism that adjusts a position of the visible light blocking portion, the visible light blocking portion transmitting the irradiated radiation and blocking the illuminated visible light, wherein, in a case in which the radiation blocking unit is attached to the radiographic imaging system, the position of the radiation blocking portion and the position of the visible light blocking portion are adjustable such that the incidence region of the radiation on the object table surface, irradiated through the through portions and the visible light blocking portion, coincides with the incidence region of the visible light on the object table surface, illuminated through the through portions and the radiation blocking portion.

2. The radiation blocking unit according to claim 1, wherein an overlapping incidence region, in which the incidence region of the radiation and the incidence region of the visible light overlap, corresponds to an observation region of an examination object placed on the object table surface.

3. The radiation blocking unit according to claim 1, wherein the attachment member is formed of a rolled steel plate that blocks the radiation from the radiation source and the visible light from the visible light source.

4. The radiation blocking unit according to claim 1, wherein the radiation blocking portion is formed of lead glass and the visible light blocking portion is formed of carbon-glass fiber.

5. A radiographic imaging apparatus comprising:
an object table that has an object table surface;
a radiation source disposed above the object table surface;
a radiation emitting section that controls the emission of radiation from the radiation source;
a visible light source disposed above the object table surface at a position different from that of the radiation source;
a visible light emitting section that controls the emission of visible light from the visible light source;
a blocking plate, disposed between the object table surface and the radiation source, that defines an incidence region of the radiation from the radiation source on the object table surface;
an optical mirror that coincides visible light illuminated from the visible light source with the incidence region of the radiation;
a blocking plate moving section that moves the blocking plate in a direction intersecting the direction in which the radiation is emitted so as to move the incidence region of the radiation on the object table surface; and
a radiation blocking unit including an attachment member that is detachably attachable between the blocking plate and the object table surface, the attachment member being made of a material, and having a thickness, such that the attachment member transmits nether radiation, nor visible light, the attachment member having one or more through portions that define an incidence region of the radiation and an incidence region of the visible light on the object table surface, the attachment member including:
a radiation blocking portion, disposed on the attachment member via a position adjusting mechanism that adjusts a position of the radiation blocking portion, the radiation blocking portion transmitting the illuminated visible light and blocking the irradiated radiation, and
a visible light blocking portion, disposed on the attachment member via a position adjusting mechanism that adjusts a position of the visible light blocking portion, the visible light blocking portion transmitting the irradiated radiation blocking the illuminated visible light,
wherein, in a case in which the radiation blocking unit is attached to the radiographic imaging apparatus, the position of the radiation blocking portion and the position of the visible light blocking portion are adjustable such that the incidence region of the radiation on the object table surface, irradiated through the through portions and the visible light blocking portion, coincides with the incidence region of the visible light on the object table surface, illuminated through the through portions and the radiation blocking portion.

6. The radiographic imaging apparatus according to claim 5, further comprising a biopsy unit, disposed between the object table surface and the blocking plate, that examines tissue.

7. The radiographic imaging apparatus according to claim 5, further comprising a compression plate disposed between the object table surface and the blocking plate, that compresses an examination object.

* * * * *